(12) United States Patent
Wright et al.

(10) Patent No.: US 9,527,747 B2
(45) Date of Patent: Dec. 27, 2016

(54) EXTRACTION AND SEQUESTRATION OF CARBON DIOXIDE

(71) Applicant: Carbon Sink, Inc., Huntington, NY (US)

(72) Inventors: Allen B. Wright, Tucson, AZ (US); Klaus S. Lackner, Dobbs Ferry, NY (US)

(73) Assignee: Carbon Sink, Inc., Huntington, NY (US)

( * ) Notice: Subject to any disclaimer, the term of this patent is extended or adjusted under 35 U.S.C. 154(b) by 0 days.

(21) Appl. No.: 14/561,831

(22) Filed: Dec. 5, 2014

(65) Prior Publication Data

US 2015/0274536 A1    Oct. 1, 2015

Related U.S. Application Data

(63) Continuation of application No. 14/257,698, filed on Apr. 21, 2014, now abandoned, which is a (Continued)

(51) Int. Cl.
*B01D 53/02* (2006.01)
*C01B 31/20* (2006.01)
(Continued)

(52) U.S. Cl.
CPC .............. *C01B 31/20* (2013.01); *A01K 67/033* (2013.01); *A01M 1/023* (2013.01); *A01N 59/04* (2013.01);
(Continued)

(58) Field of Classification Search
CPC ...... A01K 67/033; A01M 1/023; A01N 59/04; B01D 2252/00; B01D 2252/103; B01D 2252/204; B01D 2257/302; B01D 2257/402; B01D 2257/404; B01D 2257/504; B01D 2259/40086; B01D 2259/4009; B01D 2259/4145; B01D 53/02; B01D 53/0462; B01D 53/1475; B01D 53/22; B01D 53/62; B01D 53/96; B01D 61/445; B01D 2253/102; B01D 2253/206; B65D 88/745; C01B 31/20; G06Q 30/018; Y02C 10/04; Y02C 10/08; Y02C 10/10; Y02C 20/10; Y02P 20/152; Y02P 20/153

See application file for complete search history.

(56) References Cited

U.S. PATENT DOCUMENTS

| | | | |
|---|---|---|---|
| 1,031,799 A | | 7/1912 | MacKay |
| 1,296,889 A | | 3/1919 | White |

(Continued)

FOREIGN PATENT DOCUMENTS

| | | |
|---|---|---|
| CA | 1212522 | 10/1986 |
| CA | 1236877 | 5/1988 |

(Continued)

OTHER PUBLICATIONS

Office action dated Feb. 25, 2015 for U.S. Appl. No. 13/550,691.
(Continued)

*Primary Examiner* — Christopher P Jones
(74) *Attorney, Agent, or Firm* — Wilson Sonsini Goodrich & Rosati

(57) ABSTRACT

The present disclosure provides a method and apparatus for extracting carbon dioxide ($CO_2$) from a fluid stream and for delivering that extracted $CO_2$ to controlled environments for utilization by a secondary process. Various extraction and delivery methods are disclosed specific to certain secondary uses, included the attraction of $CO_2$ sensitive insects, the ripening and preservation of produce, and the neutralization of brine.

25 Claims, 7 Drawing Sheets

Related U.S. Application Data continuation of application No. 13/737,818, filed on Jan. 9, 2013, now abandoned, which is a continuation of application No. 12/389,213, filed on Feb. 19, 2009, now abandoned.

(60) Provisional application No. 61/029,831, filed on Feb. 19, 2008, provisional application No. 61/074,972, filed on Jun. 23, 2008, provisional application No. 61/079,776, filed on Jul. 10, 2008.

(51) Int. Cl.

| | | |
|---|---|---|
| *A01N 59/04* | (2006.01) | |
| *B01D 53/62* | (2006.01) | |
| *B01D 53/96* | (2006.01) | |
| *B01D 61/44* | (2006.01) | |
| *B01D 53/14* | (2006.01) | |
| *A01K 67/033* | (2006.01) | |
| *A01M 1/02* | (2006.01) | |
| *B01D 53/22* | (2006.01) | |
| *B65D 88/74* | (2006.01) | |
| *G06Q 30/00* | (2012.01) | |
| *B01D 53/04* | (2006.01) | |

(52) U.S. Cl.
CPC ........... *B01D 53/02* (2013.01); *B01D 53/1475* (2013.01); *B01D 53/22* (2013.01); *B01D 53/62* (2013.01); *B01D 53/96* (2013.01); *B01D 61/445* (2013.01); *B65D 88/745* (2013.01); *G06Q 30/018* (2013.01); *B01D 53/0462* (2013.01); *B01D 2252/00* (2013.01); *B01D 2252/103* (2013.01); *B01D 2252/204* (2013.01); *B01D 2253/102* (2013.01); *B01D 2253/206* (2013.01); *B01D 2257/302* (2013.01); *B01D 2257/402* (2013.01); *B01D 2257/404* (2013.01); *B01D 2257/504* (2013.01); *B01D 2259/4009* (2013.01); *B01D 2259/40086* (2013.01); *B01D 2259/4145* (2013.01); *Y02C 10/04* (2013.01); *Y02C 10/08* (2013.01); *Y02C 10/10* (2013.01); *Y02C 20/10* (2013.01); *Y02P 20/152* (2015.11); *Y02P 20/153* (2015.11)

(56) References Cited

U.S. PATENT DOCUMENTS

| | | |
|---|---|---|
| 1,482,367 A | 1/1924 | Elledge |
| 2,718,454 A | 9/1955 | Wylie |
| 2,796,145 A | 6/1957 | King |
| 2,922,489 A | 1/1960 | Lee |
| 3,024,207 A | 3/1962 | Shaw et al. |
| 3,063,195 A | 11/1962 | Ravich |
| 3,111,485 A | 11/1963 | Kunin |
| 3,282,831 A | 11/1966 | Hamm |
| 3,294,488 A | 12/1966 | Dunlop et al. |
| 3,318,588 A | 5/1967 | Russell et al. |
| 3,330,750 A | 7/1967 | McRae et al. |
| 3,344,050 A | 9/1967 | Mayland et al. |
| 3,466,019 A | 9/1969 | Priestley |
| 3,466,138 A | 9/1969 | Spiegler et al. |
| 3,470,708 A | 10/1969 | Weil et al. |
| 3,489,506 A | 1/1970 | Galstaun et al. |
| 3,498,026 A | 3/1970 | Messinger et al. |
| 3,554,691 A | 1/1971 | Kuo et al. |
| 3,556,716 A | 1/1971 | Pollio et al. |
| 3,561,926 A | 2/1971 | McElroy |
| 3,594,989 A | 7/1971 | Bastiaans |
| 3,627,478 A | 12/1971 | Tepper |
| 3,627,703 A | 12/1971 | Kojima |
| 3,645,072 A | 2/1972 | Clapham |
| 3,691,109 A | 9/1972 | Larsen |
| 3,710,778 A | 1/1973 | Cornelius |
| 3,712,025 A | 1/1973 | Wallace |
| 3,727,375 A | 4/1973 | Wallace |
| 3,833,710 A | 9/1974 | Deschamps et al. |
| 3,841,558 A | 10/1974 | Fowler et al. |
| 3,848,577 A | 11/1974 | Storandt |
| 3,865,924 A | 2/1975 | Gidaspow et al. |
| 3,876,565 A | 4/1975 | Takashima et al. |
| 3,876,738 A | 4/1975 | Marinaccio et al. |
| 3,880,981 A | 4/1975 | Garingarao et al. |
| 3,891,411 A | 6/1975 | Meyer |
| 3,907,967 A | 9/1975 | Hiss |
| 3,915,822 A | 10/1975 | Veltman |
| 3,948,627 A | 4/1976 | Schwarz et al. |
| 3,981,698 A | 9/1976 | Leppard |
| 4,012,206 A | 3/1977 | Macriss et al. |
| 4,047,894 A | 9/1977 | Kuhl |
| 4,140,602 A | 2/1979 | Lewis et al. |
| 4,167,551 A | 9/1979 | Tamura et al. |
| 4,197,421 A | 4/1980 | Steinberg |
| 4,238,305 A | 12/1980 | Gancy et al. |
| 4,239,515 A | 12/1980 | Yanagioka et al. |
| 4,246,241 A | 1/1981 | Mathur et al. |
| 4,249,317 A | 2/1981 | Murdoch |
| 4,296,050 A | 10/1981 | Meier |
| 4,321,410 A | 3/1982 | Ono et al. |
| 4,336,227 A | 6/1982 | Koyama et al. |
| 4,340,480 A | 7/1982 | Pall et al. |
| 4,398,927 A | 8/1983 | Asher et al. |
| 4,409,006 A | 10/1983 | Mattia |
| 4,425,142 A | 1/1984 | Mann |
| 4,436,707 A | 3/1984 | Karwat |
| 4,475,448 A | 10/1984 | Shoaf et al. |
| 4,497,641 A | 2/1985 | Brown, Jr. et al. |
| 4,511,375 A | 4/1985 | BeVier |
| 4,528,248 A | 7/1985 | Galbraith et al. |
| 4,543,112 A | 9/1985 | Ackley et al. |
| 4,566,221 A | 1/1986 | Kossin |
| 4,569,150 A | 2/1986 | Carlson et al. |
| 4,592,817 A | 6/1986 | Chlanda et al. |
| 4,594,081 A | 6/1986 | Kroll et al. |
| 4,608,140 A | 8/1986 | Goldstein |
| 4,678,648 A | 7/1987 | Wynn |
| 4,711,097 A | 12/1987 | Besik |
| 4,711,645 A | 12/1987 | Kumar |
| 4,729,883 A | 3/1988 | Lam et al. |
| 4,735,603 A | 4/1988 | Goodson et al. |
| 4,770,777 A | 9/1988 | Steadly et al. |
| 4,804,522 A | 2/1989 | Hass |
| 4,810,266 A | 3/1989 | Zinnen et al. |
| 4,861,360 A | 8/1989 | Apffel |
| 4,869,894 A | 9/1989 | Wang et al. |
| 4,899,544 A | 2/1990 | Boyd |
| 4,906,263 A | 3/1990 | Von Blucher et al. |
| 4,941,898 A | 7/1990 | Kimura |
| 4,946,620 A | 8/1990 | Kadono et al. |
| 4,953,544 A | 9/1990 | Hansen et al. |
| 4,957,519 A | 9/1990 | Chen |
| 4,980,098 A | 12/1990 | Connery |
| 5,069,688 A | 12/1991 | Wells |
| 5,070,664 A | 12/1991 | Groh et al. |
| 5,170,633 A | 12/1992 | Kaplan |
| 5,180,750 A | 1/1993 | Sugaya et al. |
| 5,203,411 A | 4/1993 | Dawe et al. |
| 5,215,662 A | 6/1993 | Johnson et al. |
| 5,253,682 A | 10/1993 | Hackette et al. |
| 5,277,915 A | 1/1994 | Provonchee et al. |
| 5,281,254 A | 1/1994 | Birbara et al. |
| 5,304,234 A | 4/1994 | Takatsuka et al. |
| 5,308,466 A | 5/1994 | Ganzi et al. |
| 5,316,637 A | 5/1994 | Ganzi et al. |
| 5,318,758 A | 6/1994 | Fujii et al. |
| 5,328,851 A | 7/1994 | Zaromb |
| 5,344,627 A | 9/1994 | Fujii et al. |
| 5,385,610 A | 1/1995 | Deerer et al. |
| 5,389,257 A | 2/1995 | Todd et al. |
| 5,401,475 A | 3/1995 | Ayala et al. |
| 5,409,508 A | 4/1995 | Erickson |

(56) References Cited

U.S. PATENT DOCUMENTS

| | | |
|---|---|---|
| 5,414,957 A | 5/1995 | Kenney |
| 5,443,740 A | 8/1995 | Schmitt |
| 5,454,189 A | 10/1995 | Graham et al. |
| 5,520,894 A | 5/1996 | Heesink et al. |
| 5,525,237 A | 6/1996 | Birbara et al. |
| 5,535,989 A | 7/1996 | Sen |
| 5,658,372 A | 8/1997 | Gadkaree |
| 5,659,974 A | 8/1997 | Graeff |
| 5,682,709 A | 11/1997 | Erickson |
| 5,711,770 A | 1/1998 | Malina |
| 5,747,042 A | 5/1998 | Choquet |
| 5,756,207 A | 5/1998 | Clough et al. |
| 5,779,767 A | 7/1998 | Golden et al. |
| 5,788,826 A | 8/1998 | Nyberg |
| 5,792,440 A | 8/1998 | Huege |
| 5,797,979 A | 8/1998 | Quinn |
| 5,833,747 A | 11/1998 | Bleakley et al. |
| 5,876,488 A | 3/1999 | Birbara et al. |
| 5,887,547 A | 3/1999 | Caveny et al. |
| 5,914,455 A | 6/1999 | Jain et al. |
| 5,917,136 A | 6/1999 | Gaffney et al. |
| 5,934,379 A | 8/1999 | Ostlyngen et al. |
| 5,955,043 A | 9/1999 | Neuman et al. |
| 5,962,545 A | 10/1999 | Chaudhary et al. |
| 5,972,080 A | 10/1999 | Nagata |
| 5,980,611 A | 11/1999 | Kumar et al. |
| 6,004,381 A | 12/1999 | Rohrbach et al. |
| 6,027,552 A | 2/2000 | Ruck et al. |
| 6,048,509 A | 4/2000 | Kawai et al. |
| 6,083,740 A | 7/2000 | Kodo et al. |
| 6,117,404 A | 9/2000 | Mimura et al. |
| 6,136,075 A | 10/2000 | Bragg et al. |
| 6,158,623 A | 12/2000 | Benavides et al. |
| 6,180,012 B1 | 1/2001 | Rongved |
| 6,200,543 B1 | 3/2001 | Allebach et al. |
| 6,209,256 B1 * | 4/2001 | Brittin .................. A01M 1/023 43/107 |
| 6,214,303 B1 | 4/2001 | Hoke et al. |
| 6,221,225 B1 | 4/2001 | Mani |
| 6,228,145 B1 | 5/2001 | Falk-Pedersen et al. |
| 6,237,284 B1 | 5/2001 | Erickson |
| 6,279,576 B1 | 8/2001 | Lambert |
| 6,284,021 B1 | 9/2001 | Lu et al. |
| 6,306,803 B1 | 10/2001 | Tazaki |
| 6,316,668 B1 | 11/2001 | King et al. |
| 6,322,612 B1 | 11/2001 | Sircar et al. |
| 6,334,886 B1 | 1/2002 | Barnes, Jr. et al. |
| 6,364,938 B1 | 4/2002 | Birbara et al. |
| 6,402,819 B1 | 6/2002 | De Ruiter et al. |
| 6,500,236 B2 | 12/2002 | Suzuki et al. |
| 6,503,957 B1 | 1/2003 | Bernatowicz et al. |
| 6,526,699 B1 | 3/2003 | Foglio |
| 6,547,854 B1 | 4/2003 | Gray et al. |
| 6,565,627 B1 | 5/2003 | Golden et al. |
| 6,582,498 B1 | 6/2003 | Sass et al. |
| 6,617,014 B1 | 9/2003 | Thomson |
| 6,632,848 B2 | 10/2003 | Sugaya |
| 6,645,272 B2 | 11/2003 | Lemaire et al. |
| 6,716,888 B2 | 4/2004 | Bernatowicz et al. |
| 6,755,892 B2 | 6/2004 | Nalette et al. |
| 6,814,021 B1 | 11/2004 | Turkewitz et al. |
| 6,830,596 B1 | 12/2004 | Deckman et al. |
| 6,863,713 B1 | 3/2005 | Ghosal et al. |
| 6,890,497 B2 | 5/2005 | Rau et al. |
| 6,908,497 B1 | 6/2005 | Sirwardane |
| 6,969,466 B1 | 11/2005 | Starner |
| 7,067,456 B2 | 6/2006 | Fan et al. |
| 7,132,090 B2 | 11/2006 | Dziedzic et al. |
| 7,270,796 B2 | 9/2007 | Kemp et al. |
| 7,343,341 B2 | 3/2008 | Sandor et al. |
| 7,364,608 B2 | 4/2008 | Tanahashi et al. |
| 7,384,621 B2 | 6/2008 | Stevens et al. |
| 7,415,418 B2 | 8/2008 | Zimmerman |
| 7,420,004 B2 | 9/2008 | Hardy et al. |
| 7,604,787 B2 | 10/2009 | Maroto-Valer et al. |
| 7,655,069 B2 | 2/2010 | Wright et al. |
| 7,699,909 B2 | 4/2010 | Lackner et al. |
| 7,708,806 B2 | 5/2010 | Wright et al. |
| 7,776,296 B2 | 8/2010 | Sarlis |
| 7,795,175 B2 | 9/2010 | Olah et al. |
| 7,833,328 B2 | 11/2010 | Lackner et al. |
| 7,993,432 B2 | 8/2011 | Wright et al. |
| 8,083,836 B2 | 12/2011 | Wright et al. |
| 8,088,197 B2 | 1/2012 | Wright et al. |
| 8,133,305 B2 | 3/2012 | Lackner et al. |
| 8,221,527 B1 | 7/2012 | Wright et al. |
| 8,246,723 B2 | 8/2012 | Wright et al. |
| 8,262,774 B2 | 9/2012 | Liu |
| 8,273,160 B2 | 9/2012 | Wright et al. |
| 8,337,589 B2 | 12/2012 | Wright et al. |
| 8,702,847 B2 | 4/2014 | Lackner et al. |
| 8,715,393 B2 | 5/2014 | Wright et al. |
| 8,999,279 B2 | 4/2015 | Wright et al. |
| 9,205,372 B2 | 12/2015 | Wright et al. |
| 9,266,051 B2 | 2/2016 | Wright et al. |
| 9,266,052 B2 | 2/2016 | Wright et al. |
| 2001/0004895 A1 | 6/2001 | Preiss |
| 2001/0009124 A1 | 7/2001 | Suzuki et al. |
| 2001/0022952 A1 | 9/2001 | Rau et al. |
| 2002/0083833 A1 | 7/2002 | Nalette et al. |
| 2002/0102674 A1 | 8/2002 | Anderson |
| 2002/0178925 A1 | 12/2002 | Mimura et al. |
| 2003/0022948 A1 | 1/2003 | Seiki et al. |
| 2003/0024686 A1 | 2/2003 | Ouellette |
| 2003/0041733 A1 | 3/2003 | Seguin et al. |
| 2003/0145726 A1 | 8/2003 | Gueret et al. |
| 2003/0167692 A1 | 9/2003 | Jewell et al. |
| 2003/0205692 A1 | 11/2003 | Fleming et al. |
| 2003/0220188 A1 | 11/2003 | Marand et al. |
| 2004/0031424 A1 | 2/2004 | Pope |
| 2004/0069144 A1 | 4/2004 | Wegeng et al. |
| 2004/0103831 A1 | 6/2004 | Pope |
| 2004/0134353 A1 | 7/2004 | Gillingham et al. |
| 2004/0195115 A1 | 10/2004 | Colombo |
| 2004/0213705 A1 | 10/2004 | Blencoe et al. |
| 2004/0219090 A1 | 11/2004 | Dziedzic et al. |
| 2005/0011770 A1 | 1/2005 | Katsuyoshi et al. |
| 2005/0063956 A1 | 3/2005 | Bernklau et al. |
| 2005/0092176 A1 | 5/2005 | Ding et al. |
| 2005/0095486 A1 | 5/2005 | Hamamoto et al. |
| 2005/0204915 A1 | 9/2005 | Sammons et al. |
| 2005/0252215 A1 | 11/2005 | Beaumont |
| 2005/0269094 A1 | 12/2005 | Harris |
| 2005/0279095 A1 | 12/2005 | Goldman |
| 2006/0013963 A1 | 1/2006 | Thomson |
| 2006/0042209 A1 | 3/2006 | Dallas et al. |
| 2006/0051274 A1 | 3/2006 | Wright et al. |
| 2006/0150811 A1 | 7/2006 | Callahan et al. |
| 2006/0186562 A1 | 8/2006 | Wright et al. |
| 2006/0249020 A1 | 11/2006 | Tonkovich et al. |
| 2006/0289003 A1 | 12/2006 | Lackner et al. |
| 2007/0004023 A1 | 1/2007 | Trachtenberg |
| 2007/0089605 A1 | 4/2007 | Lampinen |
| 2007/0149398 A1 | 6/2007 | Jones et al. |
| 2007/0187247 A1 | 8/2007 | Lackner et al. |
| 2007/0199448 A1 | 8/2007 | Yates et al. |
| 2007/0217982 A1 | 9/2007 | Wright et al. |
| 2008/0008793 A1 | 1/2008 | Forsyth et al. |
| 2008/0025893 A1 | 1/2008 | Asprion et al. |
| 2008/0031801 A1 | 2/2008 | Lackner et al. |
| 2008/0087165 A1 | 4/2008 | Wright et al. |
| 2008/0276804 A1 | 11/2008 | Sayari et al. |
| 2008/0293976 A1 | 11/2008 | Olah et al. |
| 2009/0120288 A1 | 5/2009 | Lackner et al. |
| 2009/0130321 A1 | 5/2009 | Liu |
| 2009/0169452 A1 | 7/2009 | Constantz et al. |
| 2009/0232861 A1 | 9/2009 | Wright et al. |
| 2009/0294366 A1 | 12/2009 | Wright et al. |
| 2009/0320688 A1 | 12/2009 | Lackner et al. |
| 2010/0095842 A1 | 4/2010 | Lackner et al. |
| 2010/0105126 A1 | 4/2010 | Wright et al. |
| 2010/0116137 A1 | 5/2010 | Wright et al. |
| 2010/0319537 A1 | 12/2010 | Eisenberger et al. |
| 2011/0027157 A1 | 2/2011 | Wright et al. |

(56) References Cited

U.S. PATENT DOCUMENTS

| | | |
|---|---|---|
| 2011/0033357 A1 | 2/2011 | Wright et al. |
| 2011/0033358 A1 | 2/2011 | Wright et al. |
| 2011/0056382 A1 | 3/2011 | Lackner et al. |
| 2011/0079144 A1 | 4/2011 | Wright et al. |
| 2011/0079146 A1 | 4/2011 | Wright et al. |
| 2011/0079147 A1 | 4/2011 | Wright et al. |
| 2011/0081709 A1 | 4/2011 | Wright et al. |
| 2011/0081710 A1 | 4/2011 | Wright et al. |
| 2011/0081712 A1 | 4/2011 | Wright et al. |
| 2011/0083554 A1 | 4/2011 | Wright et al. |
| 2011/0108421 A1 | 5/2011 | Lackner et al. |
| 2011/0185897 A1 | 8/2011 | Wright et al. |
| 2011/0189075 A1 | 8/2011 | Wright et al. |
| 2011/0203174 A1 | 8/2011 | Lackner et al. |
| 2011/0203311 A1 | 8/2011 | Wright et al. |
| 2011/0206588 A1 | 8/2011 | Lackner et al. |
| 2011/0209614 A1 | 9/2011 | Wright et al. |
| 2011/0293503 A1 | 12/2011 | Wright et al. |
| 2012/0058032 A1 | 3/2012 | Lackner et al. |
| 2012/0220019 A1 | 8/2012 | Lackner et al. |
| 2012/0279397 A1 | 11/2012 | Wright et al. |
| 2012/0302469 A1 | 11/2012 | Lackner et al. |
| 2012/0304858 A1 | 12/2012 | Wright et al. |
| 2013/0115153 A1 | 5/2013 | Lackner et al. |
| 2013/0309756 A1 | 11/2013 | Wright et al. |
| 2013/0336722 A1 | 12/2013 | Wright et al. |
| 2013/0343981 A1 | 12/2013 | Wright et al. |
| 2014/0370576 A1 | 12/2014 | Wright et al. |
| 2015/0020683 A1 | 1/2015 | Wright et al. |
| 2015/0104554 A1 | 4/2015 | Wright et al. |
| 2015/0165373 A1 | 6/2015 | Lackner |

FOREIGN PATENT DOCUMENTS

| | | |
|---|---|---|
| CN | 1107078 A | 8/1995 |
| CN | 1391642 A | 1/2003 |
| DE | 4130837 A1 | 4/1992 |
| DE | 19521678 A1 | 6/1995 |
| DE | 19727295 A1 | 1/1999 |
| DE | 19830470 C1 | 11/1999 |
| DE | 20001385 U1 | 8/2000 |
| EP | 0020055 A1 | 12/1980 |
| EP | 0111911 A1 | 6/1984 |
| EP | 0254137 A1 | 1/1988 |
| EP | 0585898 | 9/1994 |
| FR | 2029424 | 10/1970 |
| GB | 1004046 | 9/1965 |
| GB | 1031799 | 6/1966 |
| GB | 1109439 | 4/1968 |
| GB | 1204781 | 9/1970 |
| GB | 1296889 | 11/1972 |
| GB | 1520110 | 10/1974 |
| GB | 2288143 A | 10/1995 |
| JP | 58-122022 A | 7/1983 |
| JP | 61-072035 A | 4/1986 |
| JP | 61-227822 A | 10/1986 |
| JP | 61-254220 A | 11/1986 |
| JP | 61-254221 | 11/1986 |
| JP | 61-280217 | 12/1986 |
| JP | 63-012323 A | 1/1988 |
| JP | 63-012324 A | 1/1988 |
| JP | 63-016032 A | 1/1988 |
| JP | 63-069525 A | 3/1988 |
| JP | 63-069527 A | 3/1988 |
| JP | 1208310 | 8/1989 |
| JP | 1305809 A | 12/1989 |
| JP | 2 187153 A | 7/1990 |
| JP | 3245811 A | 11/1991 |
| JP | H 04171021 A | 6/1992 |
| JP | 04-200720 | 7/1992 |
| JP | H 05-57182 | 3/1993 |
| JP | 06-071137 A | 3/1994 |
| JP | 06-253682 A | 9/1994 |
| JP | H 09276648 A | 10/1997 |
| JP | 10-057745 | 3/1998 |
| JP | 2000-051634 | 2/2000 |
| JP | 2000-107895 | 4/2000 |
| JP | 2004-089770 | 3/2004 |
| JP | 2004-261757 | 9/2004 |
| JP | 2006-266583 A | 10/2006 |
| JP | 2006-340683 | 12/2006 |
| JP | 2007-190529 A | 8/2007 |
| JP | 2008-116193 A | 5/2008 |
| JP | 2011-516107 A | 5/2011 |
| KR | 2003-0012224 A | 2/2003 |
| RU | 2097115 C1 | 11/1997 |
| SU | 511963 A1 | 4/1976 |
| SU | 715120 A1 | 2/1980 |
| SU | 1828406 A3 | 7/1993 |
| WO | WO 94/13386 A1 | 6/1994 |
| WO | WO 98/16296 A1 | 4/1998 |
| WO | WO 98/17388 A1 | 4/1998 |
| WO | WO 98/22173 A1 | 5/1998 |
| WO | WO 00/50154 A1 | 8/2000 |
| WO | WO 00/76633 A1 | 12/2000 |
| WO | WO 01/21269 A2 | 3/2001 |
| WO | WO 01/51550 A1 | 7/2001 |
| WO | WO 01/21269 A3 | 8/2001 |
| WO | WO 2005/108297 A2 | 11/2005 |
| WO | WO 2005/108297 A3 | 1/2006 |
| WO | WO 2006/009600 A2 | 1/2006 |
| WO | WO 2006/009600 A3 | 4/2006 |
| WO | WO 2006/036396 A2 | 4/2006 |
| WO | WO 2006/036396 A3 | 8/2006 |
| WO | WO 2006/084008 A1 | 8/2006 |
| WO | WO 2007/016271 A2 | 2/2007 |
| WO | WO 2007/016274 A2 | 2/2007 |
| WO | WO 2007/016271 A3 | 3/2007 |
| WO | WO 2007/016274 A3 | 3/2007 |
| WO | WO 2007/114991 A2 | 10/2007 |
| WO | WO 2007/114991 A3 | 4/2008 |
| WO | WO 2008/042919 A2 | 4/2008 |
| WO | WO 2008/131132 A1 | 4/2008 |
| WO | WO 2008/061210 A2 | 5/2008 |
| WO | WO 2008/061210 A3 | 7/2008 |
| WO | WO 2009/149292 A1 | 12/2009 |
| WO | WO 2008/042919 A3 | 7/2010 |

OTHER PUBLICATIONS

Office action dated Mar. 6, 2015 for U.S. Appl. No. 13/733,227.
Office action dated Apr. 20, 2015 for U.S. Appl. No. 14/183,751.
U.S. Appl. No. 14/257,698, filed Apr. 21, 2014, Wright et al.
U.S. Appl. No. 14/444,882, filed Jul. 28, 2014, Lackner.
U.S. Appl. No. 14/542,120, Wright et al.
U.S. Appl. No. 14/621,931, filed Feb. 13, 2015, Wright et al.
Abstracts of Eos. Trans. AGU, 82 (47), Fall Meeting 2001; pp. 3.
Abstracts of Eos. Trans. AGU, 83 (19), Spring Meeting 2002; pp. 3.
Abstracts of Eos. Trans. AGU, 83 (47), Fall Meeting 2002; pp. 3.
Balster et al. Multi-Layer Spacer Geometries With Improved Mass Transport. Journal of membrane Science. 2006; 282:351-361.
Bituin. New Findings May Redefine Renewable Energy Debate. Access Jun. 29, 2009. found at http://www.dailycal.org/article.php?id=8559.
Canadian office action dated Oct. 19, 2012 for CA 2684280.
Canadian Official Action dated Jun. 21, 2011, Appln. No. 2,577,685.
Carbon Sequestration Could Be Employed Today to Help Alleviate Greenhouse Emissions. Accessed Jun. 29, 2009. found at http://www.earthinstitute.columbia.edu/news/2003/story06-25-03b.html.
Chinese office action dated Dec. 25, 2012 for CN Application 200780036850.5.
Chinese Official Action dated Apr. 28, 2011 Appln. No. 200780042511.8.
Chinese Official Action dated Dec. 3, 2010, Appln. No. 200780008015.
Chinese Official Action dated Jun. 13, 2011, Appln. No. 200780008015.0.
Chinese Official Action dated May 5, 2010 and Jan. 20, 2011, Application No. 200680030297.X.
Choi, et al. A new preparation for cation-exchange membrane using monomer sorption into reinforcing materials. Desalination. Mar. 22, 2002; 146:287-291.

(56) References Cited

OTHER PUBLICATIONS

Choi, et al. Characterization of LDPE/polystyrene cation exchange membranes prepared by monomer sorption and UV radiation polymerization. Journal of Membrane Science. 2003; 223:201-215.
Choi, et al. Preparation and characterization of LDPE/polyvinvylbenzyl trimethyl ammonium salts anion-exchange membrane. Journal of Membrane Science. 2003; 2001:219-231.
Cuiming, et al. Fundamental Studies of a New Hybrid (Inorganic-Organic) Positively Charged Membrane: Membrane Preparation and Characterizations. Journal of Membrane Science. 2003; 216:269-278.
Dow Chemical Company, Dowex Type 1 Strong Base Anion Resin, 1998, http://www.inaqua.de/Prod/ion/pdf en/313 UPCORE Mono A625.pdf, p. 1.
Dubey et al. Chemical Extraction of Carbon Dioxide from Air to Sustain Fossil Energy by Avoiding Climate Change. 2nd Annual Conference on Carbon Sequestration, 2003.
Dubey et al., "Extraction of Carbon Dioxide from the Atmosphere Through Engineered Chemical Sinkage", Fuel Chemistry Division Preprints, 2002; pp. 1-4.
Dubey. Science for Sustainability: From Capturing Carbon Dioxide From Air to Environmental Impact of a Hydrogen Economy. Accessed Jun. 14, 2010. found at http://www.mbari.org/seminars/2003/spring2003/apr2_dubey.html.
Elliot, et al. Compensation of Atmospheric CO2 Buildup Through Engineered Chemical Sinkage. 2001; pp. 1-8.
European examination report dated Dec. 19, 2011 for EP Application No. 08746144.8.
European office action dated May 9, 2011 for EP Application No. 08746144.8.
European office action dated Jul. 4, 2011 for EP Application No. 07758183.3.
European official action dated Jan. 19, 2010 EP Application No. 05793918.3.
European Official Action, Serial No. 06 788 685.3-1213, dated Oct. 12, 2011 (3 pages).
European search report and opinion dated Jan. 7, 2011 for EP Application No. 07864483.8.
European search report and opinion dated Apr. 20, 2011 for EP Application No. 08746144.8.
European search report and opinion dated Jun. 22, 2010 for EP Application No. 07758183.3.
European search report and opinion dated Jul. 27, 2011 for EP Application No. 07853742.0.
European search report and opinion dated Oct. 16, 2009 for EP Application No. 06788685.3.
European search report and opinion dated Dec. 21, 2011 for EP Application No. 11008476.1.
Fuertes, et al. Carbon Composite Membranes from Matrimid and Kapton Polymides for Gas Separation. Microporous and Mesoporous Materials. 1999; 33:115-125.
Hashimoto, et al. Global CO2 recycling. Zairyo to Kankyo/Corrosion Engineering. 1996; 45(10):614-620. (Abstract only).
Hensel. In the Lab. Accessed Jun. 29, 2009. found at wvvw.eponline comiarticles/53584.
Huang, et al. Method to Regenerate Ammonia for the Capture of Carbon Dioxide. Energy and Fuels. 2002; 16:904-910.
Information About: David Keith. Access Sep. 26, 2005. found at http://ideas.respec.org/e/pke74.html.
Information on David Keith. Access Jun. 14, 2010. found at http://www.ucalgary.ca/-keith/.
International Preliminary Report on Patentability dated Jan. 16, 2008 for PCT/US2006/003646.
International Preliminary Report on Patentability dated Jan. 29, 2008 for PCT/US2006/029238.
International Preliminary Report on Patentability dated Feb. 15, 2011 for PCT/US2009/053461.
International Preliminary Report on Patentability dated Feb. 20, 2007 for PCT/US2005/029584.
International Preliminary Report on Patentability dated Mar. 3, 2011 for PCT/US2009/054795.
International Preliminary Report on Patentability dated May 11, 2010 for PCT/US2008/082505.
International Preliminary Report on Patentability dated May 25, 2010 for PCT/US2007/084237.
International Preliminary Report on Patentability dated May 28, 2009 for PCT/US2007/084880.
International Preliminary Report on Patentability dated Jun. 1, 2010 for PCT/US2007/80229.
International Preliminary Report on Patentability dated Sep. 9, 2008 for PCT/US2007/063607.
International Preliminary Report on Patentability dated Oct. 20, 2008 for PCT/US2008/060672.
International Preliminary Report on Patentability dated Dec. 6, 2010 for PCT/US2009/046306.
International Search report and Written Opinion dated Jan. 27, 2009 for PCT/US2008/084237.
International Search report and Written Opinion dated Jan. 30, 2007 for PCT/US2006/029238.
International Search report and Written Opinion dated Feb. 25, 2008 for PCT/US2007/063607.
International Search report and Written Opinion dated Mar. 6, 2008 for PCT/US2007/080229.
International Search report and Written Opinion dated Apr. 23, 2008 for PCT/US2007/084880.
International search report and written opinion dated May 12, 2009 for PCT/US2009/034554.
International search report and written opinion dated May 21, 2012 for PCT/US2009/053450.
International Search report and Written Opinion dated Jun. 27, 2006 for PCT/US2006/003646.
International search report and written opinion dated Aug. 30, 2007 for PCT/US2005/032848.
International Search report and Written Opinion dated Sep. 3, 2009 for PCT/US2009/046306.
International Search report and Written Opinion dated Sep. 15, 2008 for PCT/US2008/060672.
International Search report and Written Opinion dated Sep. 25, 2009 for PCT/US2009/053461.
International Search Report and Written Opinion dated Oct. 4, 2006 for PCT/US2005/029584.
International search report and written opinion dated Nov. 17, 2010 for PCT/US2010/043133.
International Search report and Written Opinion dated Dec. 9, 2009 for PCT/US2009/054795.
International Search report and Written Opinion dated Dec. 24, 2008 for PCT/US2008/082505.
International Search Report and Written Opinion dated Nov. 24, 2010 GCC/P/2007/9020.
Israel Official Action, Application Serial No. 25585/09, dated Jun. 30, 2011.
Japanese Official Action, Application Serial No. 2008-524154, dated Feb. 16, 2011, 4 pgs.
Japanese Official Action, Application Serial No. 2008-524154, dated May 31, 2011, 3 pgs.
Japanese Official Action, Application Serial No. 2009-531567, dated Feb. 7, 2011, 4 pgs.
Keith et al., "Climate Strategy with CO2 Capture from the Air" 2005; pp. 1-43.
Keith, et al. CO2 Capture From the Air: Technology Assessment and Implications for Climate Policy. pp. 1-6.
Keith. The Carrot or the Stick: How to Build a Technology-Friendly Climate Policy in Canada. Climate Change Central Apr. 15, 2005, pp. 1-32.
Korean office action dated Nov. 20, 2012 for KR Application 10-2008-7004729.
Lackner et al., "CO2 Extraction from Air" A White Paper from Los Alamos National Labs, The Reddy Corporation International, Sourcebook, Sep. 1999.
Lackner, et al. Carbon Dioxide Extraction from Air: Is It an Option?. Proceedings of the 24th Annual Technical Conference on Coal Utilization and Fuel Systems, 1999; pp. 885-896.

(56) References Cited

OTHER PUBLICATIONS

Lackner, et al. Carbon Dioxide Extraction from Air? Arguments 2001.pp. 1-5.
Lackner, et al. Free-Market Approaches to Controlling Carbon Dioxide Emissions to the Atmosphere: A Discussion of the scientific basis. Los Alamos National Laboratory (Lackner & Ziock) & Harvard University (Wilson), pp. 1-16.
Lackner, et al. The Case for Carbon Dioxide Extraction From Air. Sourcebook, Sep. 1999; vol. 57, No. 9, pp. 6-10.
Lackner, et al., "Capturing Carbon Dioxide From Air". First National Conference on Carbon Sequestrian. 2001; pp. 1-15.
Lackner. Can Fossil Carbon Fuel the $21^{st}$ Century? International Geology Review. 2002; 44:1122-1133.
Lackner. Extraction CO2 from the Air, Lackner presentation, 12 pages.
Liang, "Carbon Dioxide Capture From Flue Gas Using Regenerable Sodium-Based Sorbents", dated Aug. 1, 2003, Department of Chemical Engineering Thesis, (137 pgs).
Liu, et al. Composite Membranes from Photochemical Synthesis of Ultrathin Polymer Films. Nature vol. 352 Jul. 4, 1991.
Mexican office action dated Oct. 29, 2012 for MX/a/2008/001054.
Mexican Official Action, Dated Feb. 2, 2011, Serial No. MX/a/2008/011464.
Mexican Official Action, Dated Jan. 24, 2011, Serial No. MX/a/2007/002019.
Mexican Official Action, Serial No. MX/a/2007/002019, dated Aug. 31, 2011 (Mexico Attorney notified Attorney of record in instant application on Sep. 22, 2011) (2 pages).
Mexican Official Action, Serial No. MX/a/2009/003500, dated Oct. 12, 2011 (3 pages).
Mizutani. Structure of Ion Exchange Membranes. Journal of Membrane Science. 1990; 49:121-144.89.
Murdoch, et al. Sabatier Methanation Reactor for Space Exploration. (2005) A Collection of Technical Papers—$1^{st}$ Space Exploration Conference: Continuing the Voyage of Discovery, 2, pp. 981-987 (Abstract only).
Office action dated Jan. 25, 2011 for U.S. Appl. No. 11/227,660.
Office action dated Jan. 27, 2010 for U.S. Appl. No. 11/227,660.
Office action dated Feb. 1, 2011 for U.S. Appl. No. 11/209,962.
Office action dated Feb. 3, 2012 for U.S. Appl. No. 13/102,915.
Office action dated Feb. 4, 2010 for U.S. Appl. No. 12/555,874.
Office action dated Feb. 11, 2011 for U.S. Appl. No. 12/638,717.
Office action dated Feb. 23, 2010 for U.S. Appl. No. 11/209,962.
Office action dated Mar. 9, 2009 for U.S. Appl. No. 11/207,236.
Office action dated Mar. 11, 2011 for U.S. Appl. No. 12/903,962.
Office action dated Mar. 11, 2011 for U.S. Appl. No. 12/903,967.
Office action dated Mar. 11, 2011 for U.S. Appl. No. 12/903,970.
Office action dated Mar. 11, 2011 for U.S. Appl. No. 12/903,974.
Office action dated Mar. 11, 2011 for U.S. Appl. No. 12/903,981.
Office action dated Mar. 14, 2012 for U.S. Appl. No. 11/209,962.
Office action dated Mar. 15, 2010 for U.S. Appl. No. 11/683,824.
Office action dated Mar. 28, 2011 for U.S. Appl. No. 12/389,213.
Office action dated Mar. 30, 2009 for U.S. Appl. No. 11/346,522.
Office action dated Apr. 6, 2011 for U.S. Appl. No. 11/996,615.
Office action dated Apr. 13, 2012 for U.S. Appl. No. 13/102,901.
Office action dated May 4, 2012 for U.S. Appl. No. 13/295,950.
Office action dated May 26, 2011 for U.S. Appl. No. 11/209,962.
Office action dated Jun. 9, 2010 for U.S. Appl. No. 11/209,962.
Office action dated Jun. 17, 2009 for U.S. Appl. No. 11/346,522.
Office action dated Jun. 28, 2010 for U.S. Appl. No. 11/683,824.
Office action dated Jul. 1, 2011 for U.S. Appl. No. 13/102,915.
Office action dated Jul. 3, 2008 for U.S. Appl. No. 11/207,236.
Office action dated Jul. 3, 2012 for U.S. Appl. No. 13/102,901.
Office action dated Jul. 16, 2012 for U.S. Appl. No. 12/389,213.
Office action dated Aug. 1, 2011 for U.S. Appl. No. 12/903,974.
Office action dated Aug. 1, 2012 for U.S. Appl. No. 12/903,877.
Office action dated Aug. 3, 2011 for U.S. Appl. No. 12/903,962.
Office action dated Aug. 3, 2012 for U.S. Appl. No. 12/903,953.
Office action dated Aug. 8, 2012 for U.S. Appl. No. 12/903,873.
Office action dated Aug. 9, 2012 for U.S. Appl. No. 12/903,894.
Office action dated Aug. 10, 2012 for U.S. Appl. No. 12/903,886.
Office action dated Aug. 13, 2012 for U.S. Appl. No. 12/903,898.
Office action dated Aug. 27, 2010 for U.S. Appl. No. 11/209,962.
Office action dated Aug. 28, 2012 for U.S. Appl. No. 12/903,868.
Office action dated Aug. 30, 2012 for U.S. Appl. No. 12/903,958.
Office action dated Sep. 10, 2012 for U.S. Appl. No. 13/058,802.
Office action dated Sep. 11, 2009 for U.S. Appl. No. 11/209,962.
Office action dated Sep. 27, 2011 for U.S. Appl. No. 12/389,213.
Office action dated Sep. 27, 2011 for U.S. Appl. No. 13/102,915.
Office action dated Sep. 29, 2011 for U.S. Appl. No. 12/615,971.
Office action dated Oct. 1, 2009 for U.S. Appl. No. 11/227,660.
Office action dated Oct. 7, 2009 for U.S. Appl. No. 11/683,824.
Office action dated Oct. 7, 2010 for U.S. Appl. No. 11/227,660.
Office action dated Nov. 3, 2011 for U.S. Appl. No. 12/274,986.
Office action dated Nov. 9, 2010 for U.S. Appl. No. 12/638,717.
Office action dated Nov. 9, 2012 for U.S. Appl. No. 13/045,317.
Office action dated Nov. 10, 2010 for U.S. Appl. No. 11/996,615.
Office action dated Nov. 19, 2010 for U.S. Appl. No. 11/683,824.
Office action dated Dec. 1, 2011 for U.S. Appl. No. 13/102,901.
Office action dated Dec. 7, 2012 for U.S. Appl. No. 13/295,950.
Office action dated Dec. 20, 2012 for U.S. Appl. No. 11/209,962.
Official Action issued in Applicants' counterpart Chinese Patent Application Serial No. 200680003905.8 dated Jun. 12, 2009.
Official Action issued in Applicants' counterpart Russian Patent Application Serial No. 2008139902 (051576) dated Feb. 4, 2011.
Official Action issued in Applicants' counterpart Russian Patent Application Serial No. 2008139902 dated Nov. 19, 2010.
Official Action issued in Applicants' counterpart Russian Patent Application Serial No. 2009116621/05 (022802) dated Jun. 1, 2011.
Official Action received in Applicants' related Australian Patent Application Serial No. 2005290082 dated Apr. 20, 2007.
Official Action received in Applicants' related Australian Patent Application Serial No. 2005290082 dated Mar. 5, 2010.
Official Action received in Applicants' related Australian Patent Application Serial No. 2005290082 dated Apr. 13, 2010.
Official Action received in Applicants' related Australian Patent Application Serial No. 2005290082 dated May 20, 2010.
Official Action received in Applicants' related Australian Patent Application Serial No. 2005290082 dated Jul. 22, 2010.
Official Action received in Applicants' related Australian Patent Application Serial No. 2007233275 dated Jan. 14, 2011.
Official Action received in Applicants' related Australian Patent Application Serial No. 2007303240 dated Feb. 9, 2011.
Official Action received in Applicants' related Australian Patent Application Serial No. 2010241388 dated Jul. 7, 2011.
Official Action received in Applicants' related Australian Patent Application Serial No. 2007319211 dated Jun. 17, 2011.
Official Action received in Applicants' related Australian Patent Application Serial No. 2007233275 dated Jun. 1, 2011.
Official Action received in Applicants' related Mexican Patent Application Serial No. MX/a/2007/009081, dated Jul. 18, 2011.
Official Action received in Applicants' related New Zealand Patent Application Serial No. 575870 dated Mar. 17, 2011 and Nov. 11, 2010.
Official Action received in Applicants' related New Zealand Patent Application Serial No. 575870 dated Jun. 27, 2011.
Official Action received in related Australian Patent Application Serial No. 2006210619 dated Mar. 1, 2010.
Researchers Explore Extracting CO2 Directly From Air. Apr. 15, 2002. found at http://www.earthvision.net/ColdFusion/News Page1.cfm?NewsID=20309.
Resume of David Keith, Academic CV, Spring 2005, 8 pgs.
Rickman. Imagine No Restriction on Fossil-Fuel Usage and No Global Warming! Accessed Jun. 29, 2009. found at http://www.lanl.govinews/releases/archive/02-028.shtml.
Russian office action dated Jan. 5, 2013 for RU Application 2008139902.
Russian Official Action + Translation, dated Feb. 11, 2010, Appln. No. 2007132880/15, (13 pgs).
Russian Official Action + Translation, dated Feb. 2, 2006, Appln. No. 2007132880/15 (035886).
Russian Official Action +Translation, dated Sep. 15, 2010 Appln. No. 2007132880/15 (035886).

(56) References Cited

OTHER PUBLICATIONS

Russian Official Action, Serial No. 2008139902/15, dated Jul. 20, 2011 (Russian Attorney notified Attorney of record in instant application on Sep. 15, 2011) (6 pages).
Russian Official Action, Serial No. 200914222/05, dated Sep. 30, 2011 (9 pages).
Sata, et al. Modification of Properties of Ion Exchange Membranes. VI. Electrodialytic Transport Properties of Cation Exchange Membranes with a Electrodeposition Layer of Cationic Polyelectrolytes. 1979, pp. 1199-1213.
Sata, et al. Modification of Properties of Ion Exchange Membranes. VII. Relative Transport Number between Various Cations of Cation Exchange Membrane Having Cationic Polyelectrolyte Layer and Mechanism of Selective Permeation of Particular Cations. 1979, pp. 2071-2085.
Sata. Modification of Properties of Ion Exchange Membranes. IV. Change of Transport Properties of Cation-Exchange Membranes by Various Polyelectrolytes. 1978, pp. 10631080.
Sata. Monovalent Cation Permselective Exchange Membrane. Apr. 15, 1972, pp. 980-982.
Singer. Americans Believe in Global Warming . . . and Psychic Powers, Astrology, and UFO's. Accessed Jun. 29, 2009. Environment & Climate News, 2002; vol. 5, No. 7. found at http://heartland.org/.
Snowpure, LLC, SnowPure Excellion Product Information and Brochure. Aug. 2009.
Strieber. New Solutions to Oil Problems, Whitley Strieber's Unknown Country, 2002, found at http://www.unknowncountry.com/news/print.phtml?id=1467.
Sun et al., "CO2 sorption in activated carbon in the presence of water", dated Feb. 9, 2007, Science Direct, Chemical Physics Letterse 437 (2000) (abstract enclosed).
US Notice of Allowance, U.S. Appl. No. 12/265,556, dated Nov. 7, 2011 (33 pages).
US Official Action, U.S. Appl. No. 11/209,962, dated Oct. 6, 2011 (24 pages).
US Official Action, U.S. Appl. No. 13/208,156, dated Oct. 26, 2011 (21 pages).
Weber, et al. The absorption of carbon dioxide by weak base ion exchange resins. Aiche Journal. Jul. 1970; 609-614. http://onlinelibrary.wiley.com/doi/10.1002/aic.690160417/pdf.
Written Public Comments on the Strategic Plan for the U.S. Climate Change Science Program, General Comments. 2003, pp. 1-160.
Yin, et al., "Absorption and steam desorption performance of weak base anion exchange resin" (1995) Hangtian Yixue Yu Yixue Gongcheng/Space Medicine and Medical Engineering, 8 (1), pp. 27-31. (Abstract only).
Zeman, et al. Capturing carbon dioxide directly from the atmosphere. World resource review. 2004; 16(2):157-172.
Astarita. Mass Transfer with Chemical Reaction. Amsterdam: Elsevier Publishing Company. 1967; 144-152.
Avgul, et al. Adsorption of acid gases by macroporous, weekly basic anion exchange resins with different functional groups. Colloid Journal of the USSR. A translation of Kolloidnyi Zhurnal. 1982; 43(6):837-842.
Belyakova, et al. Adsorption of carbon dioxide and water by macroporous anion-exchange resins. Colloid Journal of the USSR. A translation of Kolloidnyi Zhurnal. 1975; 37(3):484-487.
Besra, et al. Particle Characteristics and Their Influence on Dewatering of Kaolin, Calcite and Quartz Suspensions. Int. J. Miner. Process. 2000; 59:89-122.
Blok, et al. Hydrogen Production From Natural Gas, Sequestration of Recovered CO2 in Depleted Gas Wells and Enhanced Natural Gas Recovery. Energy. 1997; 22(2-3):161-168.
Boynton. Chemistry and Technology of Lime and Limestone. New York: Interscience Publishers. 1966; 204-206.
Desideri, et al. Performance Modelling of a Carbon Dioxide Removal System for Power Plants. Energy Conversion and Management.1999; 40:1899-1915.
Dillon, et al. Oxy-Combustion Processes for CO2 Capture From Advanced Supercritical PF and NGCC Power Plant. Greenhouse Gas Control Technologies 7, Proceedings of the 7th International Conference on Greenhouse Gas Control Technologies 5—Sep. 2004, Vancouver, Canada. 211-220.
European search report dated Feb. 28, 2014 for EP Application No. 13175213.1.
European search report partial dated Oct. 11, 2013 for EP Application No. 13175213.1.
Hanson, et al. Steam Drying and Fluidized-Bed Calcination of Lime Mud. Tappi Journal. 1993; 76(11):181-188.
Herzog, et al. Carbon Dioxide Recovery and Disposal From Large Energy Systems. Annu. Rev. Energy Environ. 1996; 21:145-166.
International preliminary report on patentability dated Nov. 7, 2006 for PCT/US2005/015453.
International preliminary report on patentability dated Nov. 7, 2006 for PCT/US2005/015454.
International search report and written opinion dated Nov. 15, 2005 for PCT/US2005/015453.
International search report and written opinion dated Dec. 21, 2005 for PCT/US2005/015454.
Keith, et al. Co2 Capture From the Air: Technology Assessment and Implications for Climate Policy. Greenhouse Gas Control Technologies 6. Proceedings of the 6th International Conference on Greenhouse Gas Control Technologies 1-4 Oct. 2002, Kyoto, Japan; 187-192.
Konno, et al. Crystallization of Aragonite in the Causticizing Reaction. Powder Technology. 2002; 123:33-39.
Meier, et al. Design and Experimental Investigation of a Horizontal Rotary Reactor for the Solar Thermal Production of Lime. Energy. 2004; 29:811-821.
Notice of allowance dated Aug. 25, 2014 for U.S. Appl. No. 13/733,227.
Office action dated Jan. 28, 2014 for U.S. Appl. No. 13/386,587.
Office action dated Jan. 29, 2014 for U.S. Appl. No. 12/996,589.
Office action dated Jun. 26, 2014 for U.S. Appl. No. 13/733,227.
Office action dated Aug. 7, 2014 for U.S. Appl. No. 13/557,701.
Office action dated Aug. 15, 2014 for U.S. Appl. No. 13/550,691.
Office action dated Aug. 30, 2013 for U.S. Appl. No. 13/796,855.
Office action dated Oct. 24, 2013 for U.S. Appl. No. 13/737,818.
Office action dated Dec. 3, 2013 for U.S. Appl. No. 13/557,701.
Office action dated Dec. 9, 2013 for U.S. Appl. No. 13/550,691.
Office action dated Dec. 12, 2013 for U.S. Appl. No. 13/733,227.
Office action dated Dec. 18, 2014 for U.S. Appl. No. 13/058,812.
Olsson, et al. Thermophysical Properties of Aqueous NaOH-H20 Solutions at High Concentrations. International Journal of Thermophysics. 1997; 18(3):779-793.
Otsuji, et al. A regenerable carbon dioxide removal and oxygen recovery system for the Japanese Experiment Module. Acta Astronaut. Jan. 1987;15(1):45-54.
Singh. Technical Note Ultrasonically Assisted Rapid Solid-Liquid Separation of Fine Clean Coal Particles. Minerals Engineering. 1999; 12(4):437-443.
Steinberg, et al. Synthetic carbonaceous fuel and feedstock using nuclear power, air and water. International Journal of Hydrogen Energy. 1977; 2:189-207.
Weimer, et al. CO2 removal and fixation solar high temperature syngas generation for fuel synthesis. Energy Conyers. Mgmt. 1997; 38:S379-S384.
White, et al. Separation and capture of CO2 from large stationary sources and sequestration in geological formations—coalbeds and deep saline aquifers. J Air Waste Manag Assoc. Jun. 2003;53(6):645-715.
Zsako, et al Use of Thermal Analysis in the Study of Sodium Carbonate Causticization by Means of Dolomitic Lime. Journal of Thermal Analysis. 1998; 53:323-331.
U.S. Appl. No. 14/986,830, filed Jan. 4, 2016, Wright et al.
U.S. Appl. No. 15/046,621, filed Feb. 18, 2016, Wright et al.
U.S. Appl. No. 15/133,513, filed Apr. 20, 2016, Wright et al.
Notice of allowance dated Oct. 6, 2015 for U.S. Appl. No. 14/183,751.
Notice of allowance dated Oct. 15, 2015 for U.S. Appl. No. 13/733,227.

(56) References Cited

OTHER PUBLICATIONS

Office action dated Jan. 29, 2016 for U.S. Appl. No. 14/444,882.
Office action dated Mar. 18, 2016 for U.S. Appl. No. 13/058,812.
Office action dated Mar. 21, 2016 for U.S. Appl. No. 14/163,559.
Co-pending U.S. Appl. No. 15/243,806, filed Aug. 22, 2016.
Office action dated Aug. 3, 2016 for U.S. Appl. No. 14/163,559.
Office action dated Nov. 3, 2016 for U.S. Appl. No. 13/058,812.

* cited by examiner

EXTRACTION AND SEQUESTRATION OF CARBON DIOXIDE

CROSS-REFERENCE TO RELATED APPLICATIONS

This application is a Continuation application of U.S. application Ser. No. 14/257,698, filed Apr. 21, 2014; which is a Continuation application of U.S. application Ser. No. 13/737,818, now abandoned, filed Jan. 9, 2013; which is a Continuation Application that claims priority to U.S. application Ser. No. 12/389,213, now abandoned, filed Feb. 19, 2009; which claims priority from U.S. provisional application Ser. No. 61/029,831, filed Feb. 19, 2008, Ser. No. 61/074,972 filed Jun. 23, 2008 and Ser. No. 61/079,776 filed Jul. 10, 2008, all of which are incorporated herein by reference.

FIELD OF THE INVENTION

The present invention relates to a method and apparatus for the removal of selected gases from an environment and the disposal of the selected gases in another environment.

BACKGROUND OF THE INVENTION

The present invention in one aspect relates to removal of selected gases from the atmosphere. The invention has particular utility in connection with the extraction of carbon dioxide ($CO_2$) from the atmosphere and subsequent sequestration of the extracted $CO_2$ or conversion of the extracted $CO_2$ to useful or benign products and will be described in connection with such utilities, although other utilities are contemplated, including the extraction, sequestration or conversion of other gases from the atmosphere including $NO_x$ and $SO_2$.

There is compelling evidence of a strong correlation between the sharply increasing levels of atmospheric $CO_2$ with a commensurate increase in global surface temperatures. This effect is commonly known as Global Warming. Of the various sources of the $CO_2$ emissions, there are a vast number of small, widely distributed emitters that are impractical to mitigate at the source. Additionally, large-scale emitters such as hydrocarbon-fueled power plants are not fully protected from exhausting $CO_2$ into the atmosphere. Combined, these major sources, as well as others, have lead to the creation of a sharply increasing rate of atmospheric $CO_2$ concentration. Until all emitters are corrected at their source, other technologies are required to capture the increasing, albeit relatively low, background levels of atmospheric $CO_2$. Efforts are underway to augment existing emissions reducing technologies as well as the development of new and novel techniques for the direct capture of ambient $CO_2$. These efforts require methodologies to manage the resulting concentrated waste streams of $CO_2$ in such a manner as to prevent its reintroduction to the atmosphere.

The production of $CO_2$ occurs in a variety of industrial applications such as the generation of electricity from coal at power plants and in the use of hydrocarbons that are typically the main components of fuels that are combusted in combustion devices, such as engines. Exhaust gas discharged from such combustion devices contains $CO_2$ gas, which at present is simply released to the atmosphere. However, as greenhouse gas concerns mount, $CO_2$ emissions from all sources will have to be curtailed. For mobile sources such as motor vehicles and airplanes the best option is likely to be the collection of $CO_2$ directly from the air rather than from the mobile device in the motor vehicle or airplane. The advantage of removing $CO_2$ from air is that it eliminates the need for storing $CO_2$ on the mobile device.

Extracting carbon dioxide ($CO_2$) from ambient air would make it possible to use carbon-based fuels and deal with the associated greenhouse gas emissions after the fact. Since $CO_2$ is neither poisonous nor harmful in parts per million quantities, but creates environmental problems simply by accumulating in the atmosphere, it is possible to remove $CO_2$ from air in order to compensate for equally sized emissions elsewhere and at different times.

BRIEF SUMMARY OF THE INVENTION

The present disclosure provides a system, i.e. a method and apparatus for extracting a contaminant from a flow stream, such as ambient air or an exhaust stack, and for delivering the extracted contaminant for use in a secondary process. The present disclosure is described primarily in regards to the removal and sequestration of $CO_2$, though the apparatus and method of the present disclosure may be used with various other contaminants.

In accordance with one aspect of the present disclosure, $CO_2$ is extracted from air and the extracted $CO_2$ is delivered to a secondary process where the $CO_2$ is transformed into a useful or benign product. The $CO_2$ is delivered in whatever form is required for the secondary process, which may be gaseous, solid, or liquid $CO_2$. The secondary process may be any manufacturing, food processing, or other industrial process that uses $CO_2$, such as, machining coolant and lubricant, grit blasting, e.g. for smoothing and paint removal, cryogenic cleaning, quick freeze processes, production and use of R744 refrigerant, $CO_2$ based dry cleaning solvents, perishable shipping container pre-cooling, perishable shipping inert environment maintenance, beverage carbonation, fire suppression, plant fertilization, horticulture, agriculture, silvaculture, aquatic algae production, enhanced oil recovery, water softening, Solvay process, propellant, pressurizing gas, e.g. for aerosol cans, inflation gas, e.g. for life rafts, supercritical $CO_2$ extraction, semi conductor manufacturing, organic solvent, perfume aromatics, decaffeinating beverages, e.g. coffee and tea, supramics, pharmaceutical manufacturing, chemical production such as for urea, methanol, inorganic carbonates, organic carbonates, polyurethanes, paint pigments, foaming agents, carbon based fuels, i.e. synthetic fuels, fumigation, e.g. of grain elevators, neutralization of alkaline water, gas shield, e.g. for welding, which are given as exemplary.

A further aspect of the present disclosure provides a method and apparatus for luring $CO_2$ sensitive insects toward a specific location where a moisture sensitive $CO_2$ sorbent that is partially or fully loaded with $CO_2$ is exposed to moisture usually in excess of that present in the ambient air at the location. The sorbent may be held in place by an open basket that is protected with a roof and a floor against accidental wetting by rain.

Another aspect of the present disclosure is directed to the control of the concentration of specific gases in a closed environment. While the method and apparatus of this aspect of the present disclosure will be described with specific reference to the control of carbon dioxide in the storage, for example, of bananas, but other fruits and vegetables are also contemplated by this disclosure. The present invention provides a atmosphere-controlled environment for storing produce, wherein other parameters as well as carbon dioxide such as humidity may also be controlled, and a plurality of filters attached to the temperature controlled environment.

Yet another aspect of the present disclosure provides a system, i.e. a method and apparatus for extracting carbon dioxide ($CO_2$) from ambient air or an exhaust stack and for delivery, sequestration or conversion of the extracted $CO_2$ into useful or benign products.

The extraction of the contaminant from a gas stream in any of the aspects of the present disclosure discussed above may be accomplished by using one of a number of methods such as disclosed in the several patent applications listed in Appendix A, the contents of which are incorporated herein by reference, as well as other extraction processes described in the literature and patent art, including processes which capture $CO_2$ at the stack.

BRIEF DESCRIPTION OF THE DRAWINGS

Further features and advantages of the present invention will be seen from the following detailed description, taken in conjunction with the accompanying drawings, wherein.

DETAILED DESCRIPTION

Various methods and apparatus have been developed for removing $CO_2$ from air. For example, we have recently disclosed methods for efficiently extracting carbon dioxide ($CO_2$) from ambient air using sorbents that either physically or chemically bind and remove $CO_2$ from the air. A class of practical $CO_2$ capture sorbents include strongly alkaline hydroxide solutions such as, for example, sodium or potassium hydroxide, or a carbonate solution such as, for example, sodium or potassium carbonate brine. See for example published PCT Application PCT/US05/29979 and PCT/US06/029238. See also published PCT Application PCT/US07/802229 which describes the use of solid sorbents such as ion exchange resins for removing $CO_2$ from the air.

In broad concept, the present invention in one aspect extracts carbon dioxide from ambient air using a conventional $CO_2$ extraction method or one of the improved $CO_2$ extraction methods disclosed in our aforesaid PCT Applications, or disclosed herein, and releases at least a portion of the extracted $CO_2$ to a secondary process employing $CO_2$. The $CO_2$ also may be extracted from an exhaust at the exhaust stack.

In our co-pending U.S. application Ser. No. 11/866,326, assigned to a common assignee and incorporated by reference herein, there are provided methods and apparati for extracting carbon dioxide ($CO_2$) from ambient air and for delivering that extracted $CO_2$ to controlled environments. Specifically, the aforementioned applications disclose the delivery of $CO_2$ collected from ambient air or from exhaust gases for use in greenhouses or in algae cultures. The $CO_2$ is extracted from the gas stream by an ion exchange material that when exposed to dry air absorbs $CO_2$ that it will release at a higher partial pressure when exposed to moisture. In this process we can achieve concentration enhancements by factors of from 1 to 100.

Figure 1:
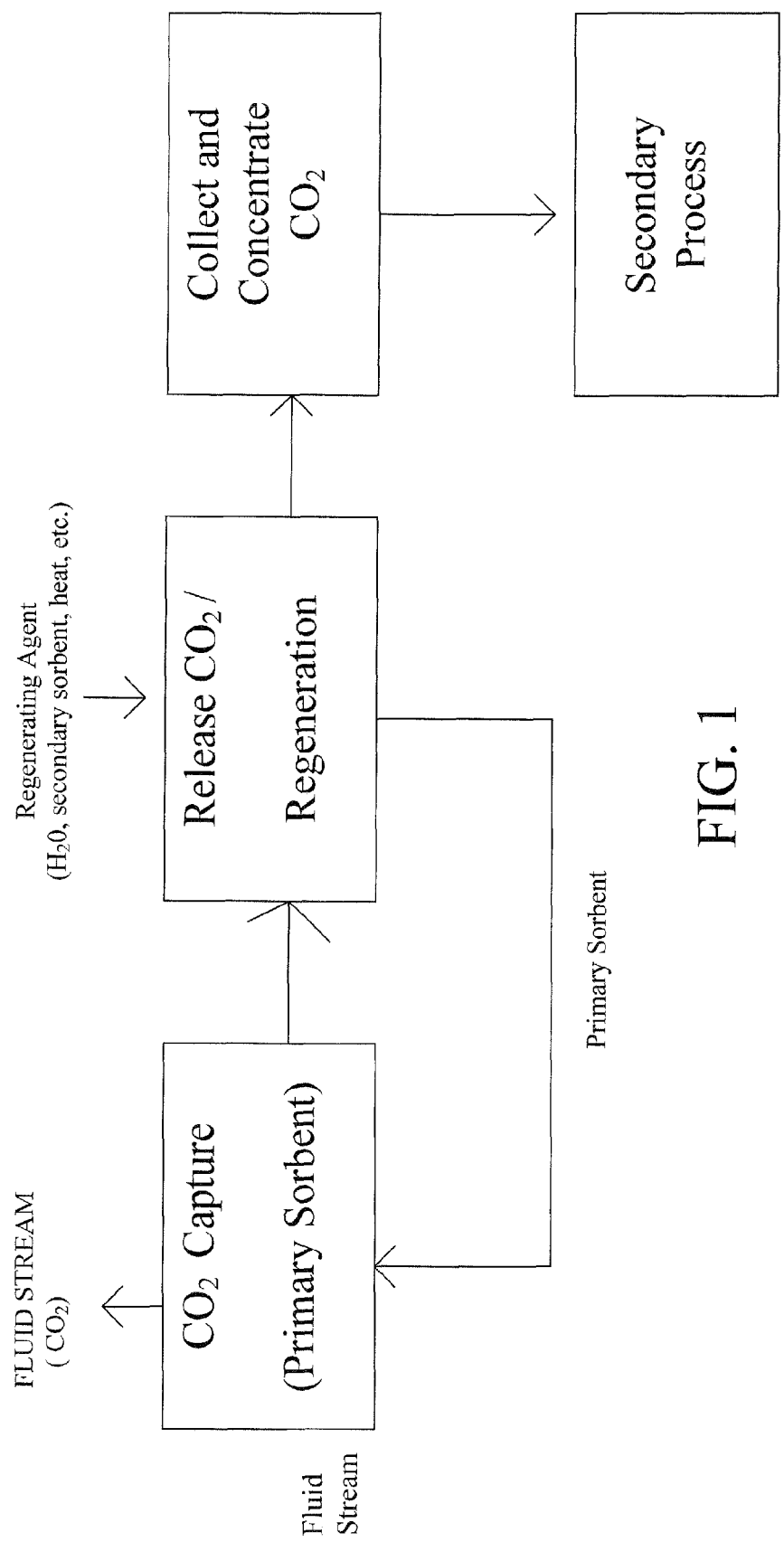
FIG. 1 is a schematic showing a system for capturing $CO_2$ in accordance with the present invention wherein $CO_2$ is delivered to a secondary process.

In a first exemplary embodiment shown in FIG. 1, the present invention provides a system for removing $CO_2$ from a fluid stream in a capture apparatus, comprising passing the fluid stream in contact with a primary sorbent to absorb $CO_2$ from the fluid stream. The fluid stream may be ambient air, a flue stream, or any other fluid stream from which the sorbent is capable of withdrawing $CO_2$. The $CO_2$ is then released by the primary sorbent and delivered to a secondary process.

The secondary process preferably is connected directly to the $CO_2$ capture apparatus to minimize transportation costs and potential losses associated therewith. Depending on the intended secondary process, the $CO_2$ may be transformed into a solid or liquid state. The $CO_2$ may further be conditioned to a specified pressure and/or temperature.

The secondary process may be any manufacturing, food processing, or other industrial process that uses $CO_2$, such as for example, machining coolant and lubricant, grit blasting, e.g. for smoothing and paint removal, cryogenic cleaning, quick freeze processes, R744 refrigerant, dry cleaning solvent, perishable shipping container pre-cooling, perishable shipping inert environment maintenance, beverage carbonation, fire suppression, plant fertilization, horticulture, agriculture, silvaculture, aquatic algae production, enhanced oil recovery, water softening, Solvay process, propellant, pressurizing gas, e.g. for aerosol cans, inflation gas, e.g. for life rafts, supercritical $CO_2$ extraction, semi conductor manufacturing, organic solvent, perfume aromatics, decaffeinating beverages, e.g. coffee and tea, supramics, pharmaceutical manufacturing, chemical production such as for urea, methanol, inorganic carbonates, organic carbonates, polyurethanes, paint pigments, foaming agents, carbon based fuels, i.e. synthetic fuels, fumigation, e.g. of grain elevators, neutralization of alkaline water, gas shield, e.g. for welding, Many other processes utilizing $CO_2$ are also possible and are deemed to be within the scope of this disclosure.

Our aforementioned commonly owned applications disclose several potential primary sorbents that may be used to capture and remove $CO_2$ from the air. In one approach to $CO_2$, capture, the sorbent is a strong base ion exchange resin that has a strong humidity function, that is to say, an ion exchange resin having the ability to take up $CO_2$ as humidity is decreased, and give up $CO_2$ as humidity is increased. Such resins may be regenerated by contact with water, humid air, or pulses of steam. In this approach the $CO_2$ is returned to a gaseous phase in a more concentrated form, and no liquid media are brought in contact with the collector material.

Other primary sorbents may be regenerated by a secondary sorbent such as weak liquid amine. This amine must be capable of pulling the $CO_2$ content of gas mixture down so that the $CO_2$ partial pressure drops to about e.g., 20 to 30 mbar. Thus it can be far weaker sorbent than the primary sorbent and this allows the use of very weak amines.

Still other sorbent materials may be regenerated by the application of heat (utilizing a thermal swing), or vacuum pressure.

Figure 2A:
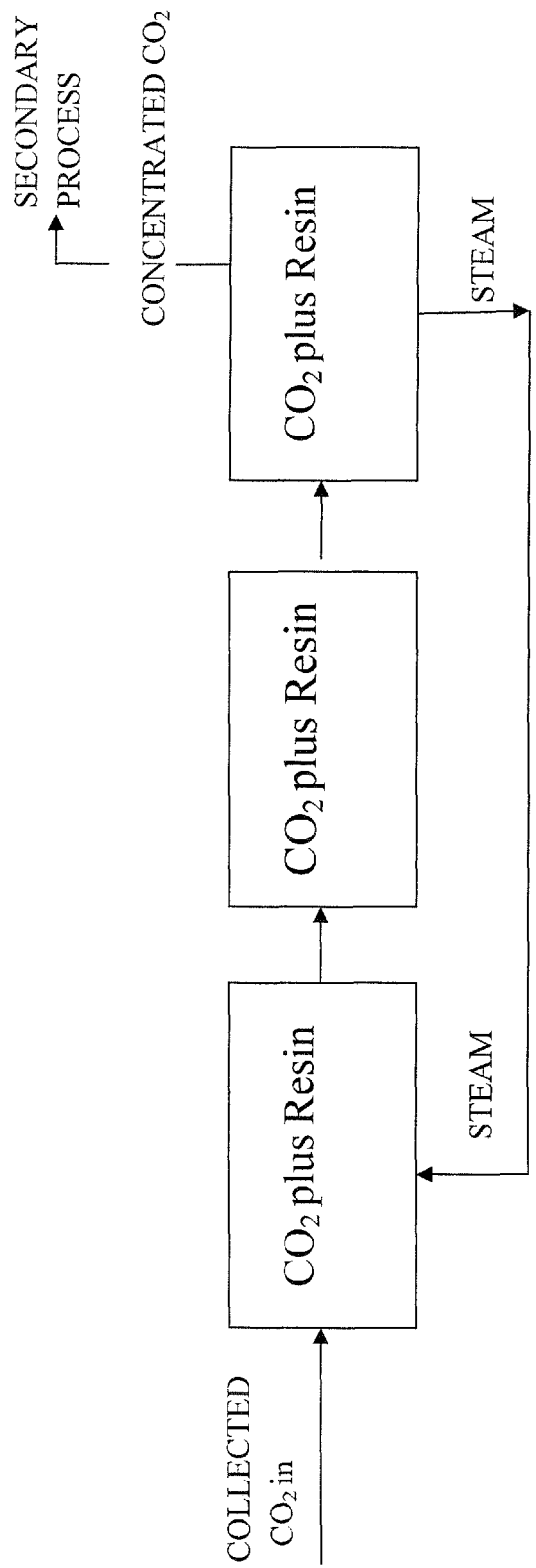
FIG. 2A is a schematic showing an ion exchange process for capturing $CO_2$ in accordance with one aspect of the present disclosure wherein multiple chambers are used in succession.
Figures 2B, 3:
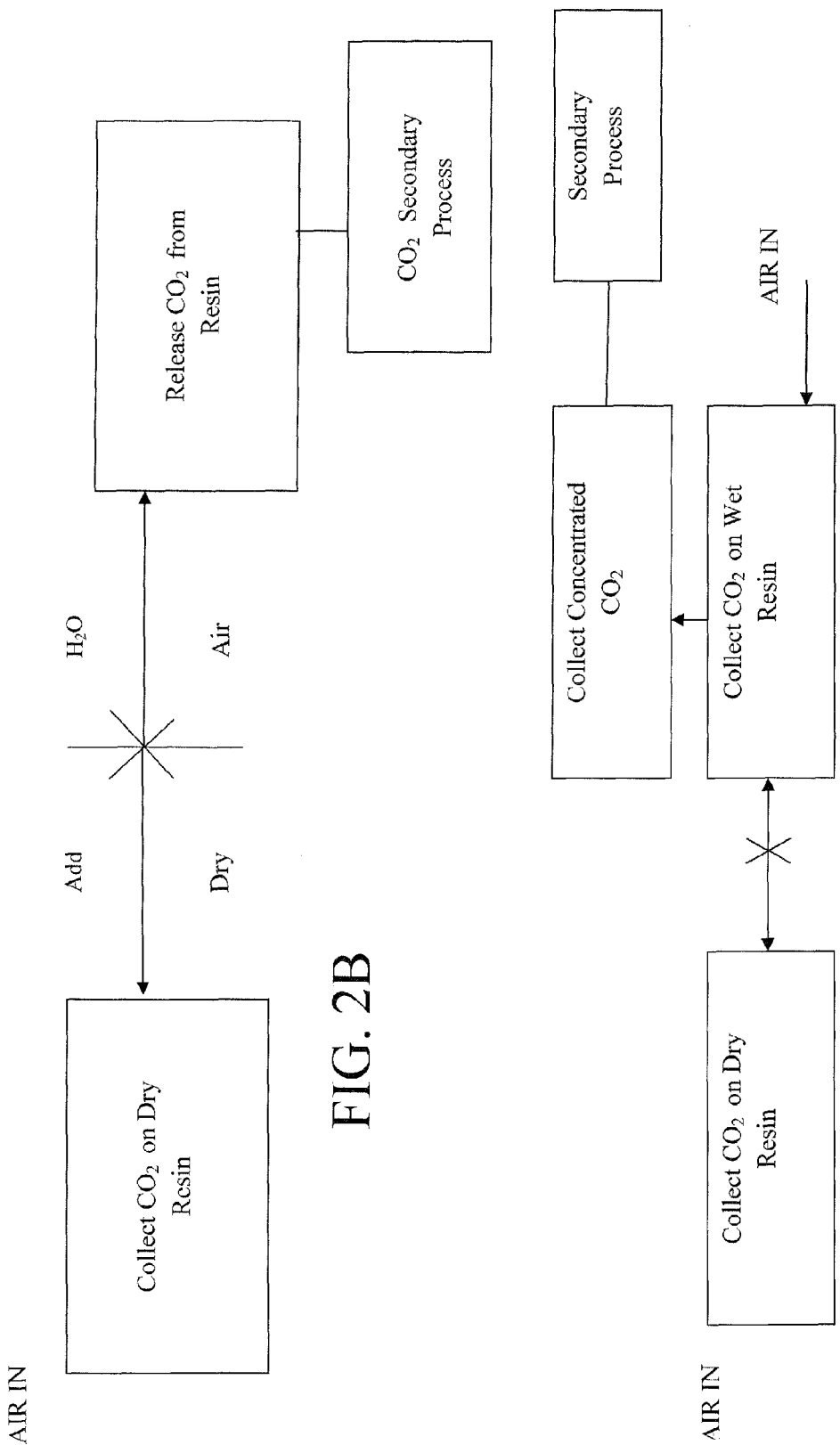
FIG. 2B is a schematic showing an ion exchange process for capturing $CO_2$ where valves are used to control flow between chambers in accordance with the present disclosure.
FIG. 3 is a schematic showing an ion exchange process for capturing $CO_2$ employing activated carbon in accordance with one aspect of the present disclosure.

In another example, $CO_2$ is captured and removed from air on a solid phase ion-exchange resin which is placed in a plurality of chambers connected in series. See FIG. 2A. The resins in the different chambers have been exposed for different length of time to the outgassing process. Resins may move from chamber to chamber, or more likely as shown in FIG. 2B, the valving is changed to take a chamber from the purged end of the chain, remove its charge and fill it with a resin which is now put on the unpurged end of the chain. The gas in each chamber is composed of water vapor, $CO_2$ and possibly an inert sweep gas. The sum of the three partial pressures monotonically declines from the upstream end of the system to the downstream end of the system. The sweep gas pressure can be reduced by increasing the flow speed, but the water vapor pressure is more or less in equilibrium with the liquid water at this point. The $CO_2$ pressure should increase in the direction of the sweep. If the water vapor is a large part of the total pressure, the water vapor pressure gradient controls the flow and it would be established by a temperature drop from one chamber to the next, while the $CO_2$ pressure will rise from one chamber to the next, as each chamber is adding some $CO_2$ to the flow. The contributions of each chamber will be limited by the rate at which the material can release $CO_2$ and the equilibrium pressure that particular resin can reach.

The following conceptually describes a $CO_2$ washing system that is based on immersing the resin into liquid water and moving the water over the resin into a separate chamber where the $CO_2$ is allowed to be released from the water.

A simple implementation is a set of chamber organized (at least logically into a circle). All but one chamber are filled with water. One chamber (n) is empty and filled with air. Initially chamber n is filled with air, and chamber n+1 is filled with water. Now water is pumped against a minimal pressure drop from chamber k to k+1. This will work for all values of k, except that k=n−1, n, n+1 are special cases which need further consideration. The water in chamber n−1 flows into chamber n, thereby pushing the air inside this chamber out. It is either released to the outside or channeled into chamber n+1 whose water content is moving into chamber n+1. The water pouring into chamber n will inundate the resin that has been replaced into this chamber. The water in chamber n+1 flows into chamber n+2, but rather than obtaining water from chamber n, it pulls in air, which may be the air that resided in chamber n, or fresh air taken from the outside.

At this point we renumber all chambers by replacing n with n−1. Thus it is again chamber n that is filled with air. We now open chamber n, and remove the regenerated resin and replace it with fully loaded resin. Before we load up chamber n, we pump the water from station n−1 to a degassing station and from there to station n+1. This water flow bypasses the currently open chamber n.

This procedure could be used with pure water, in which the process is a simple degassing, but it could also be performed with a carbonate solution which is turned into a bicarbonate and where the $CO_2$ is removed by other means. $CO_2$ removal could be based on an evacuation (which could be achieved by operating an inverted siphon), or based on electrodialysis, or involve a secondary sorbent that is far more compact and thus allows for an easier regeneration option. It also could involve precipitation of bicarbonate from the solution in a thermal swing or a thermal swing for $CO_2$ release from the mixture. The basic layout is independent of these ideas.

A variation of this idea has all chambers evacuated with the exception of chamber n−1 which is filled with water, n which is open to the air, and n+1 which is again filled with water. The nominally evacuated chambers are filled with a mixture of water vapor and $CO_2$. In this case, we pump water from chamber n−1 into n, displacing the air to the outside and immersing the resin in water. The pump does not need to do much work, because at the same time the water in chamber n+1 is sucked into chamber n+2, while chamber n+1 fills itself with air. At the end of this process chamber n+1 is filled with air and open to the outside. Chamber n is filled with water and at vacuum pressure. Chamber n+2 is filled with water and at vacuum pressure, and all other chambers are still under vacuum conditions. No net work was done, but all chambers moved by one. We can now renumber all chambers, and repeat the cycle.

In this case we use the water to stimulate the gas release and the freshly wetted resin in the last chamber is now topping off the $CO_2$ which is pumped out of this chamber, letting gas flow from all other chambers into this one. The $CO_2$ content of the water is likely to be high, however, it remains more or less constant over time as we do not extract this $CO_2$, so after some initial transients, this $CO_2$ reservoir will remain constant and not remove $CO_2$ from the resin (we ignore here some small losses to the outside air which are not completely avoidable) check valves can be installed to prevent backward flow. As a result we have a water driven implementation of the $CO_2$ release which his significantly simpler than a water vapor driven system.

Optionally, some of the water vapor may be recovered from the system during the compression stage. This will provide sufficient heat that the system can operate at slightly elevated temperatures. Indeed it is possible to use the last step of pumping out of the gas to severely cool the resin and remove all excess water.

Yet other possibilities exist. For example, it is possible to create a buffer storage for the water which makes it possible to slowly withdraw water from chamber n−1 and in a second step fill chamber n very rapidly so as to minimize the amount of time the water is in contact with air and thus can exchange gas with the outside air. The buffer itself must be able to change volume. It takes on an additional volume as it takes on the fluid from chamber n−1. It then contracts again as it pushes the same volume into chamber n. Again mechanical work is related to friction losses, inertial losses, and losses to slight pressure mismatches between the various chambers. This can be adjusted for with careful thermal management.

In yet another example $CO_2$ is captured and removed from air by employing hydrophobic activated carbon materials with strong base ion exchange resins. See FIG. 3. This latter process is based on observation that activated carbon has been observed to absorb $CO_2$ when wet, and release the absorbed $CO_2$ as it dries. This is the opposite behavior from ion exchange resins. Accordingly, this makes it possible to couple solid phase ion exchange resin extractors and activated carbon extractors in sequence. Starting with dry activated carbon and moistened resin materials air is passed through the system. As the air dries the resin, it transports the water vapor to the carbon. The resin picks up $CO_2$ as it dries, and the activated carbon picks up $CO_2$ as it accepts moisture. Once the resin is dry, the system is reversed, and fresh air is flowed through the activated carbon, and releases moisture back to the ion exchange resins. As the carbon dries it gives off $CO_2$, raising the $CO_2$ partial pressure where it can be concentrated and removed. A feature and advantage of coupling ion exchange material and activated carbon in this manner is that water is preserved, and is a simple matter of valving to reverse air flow.

Alternatively, zeolite materials may be used in place of activated carbon. By stringing several air capture devices together, the ambient $CO_2$ removed may be concentrated before passing to a secondary process.

The same ion exchange resins may be used to remove excess $CO_2$ build-up from closed containers such as storage containers for fresh fruit or vegetables, e.g., bananas, in order to maintain a maximum level of $CO_2$ in the container and avoid excessive ripening or spoilage, as will be described in greater detail below.

Figure 4:
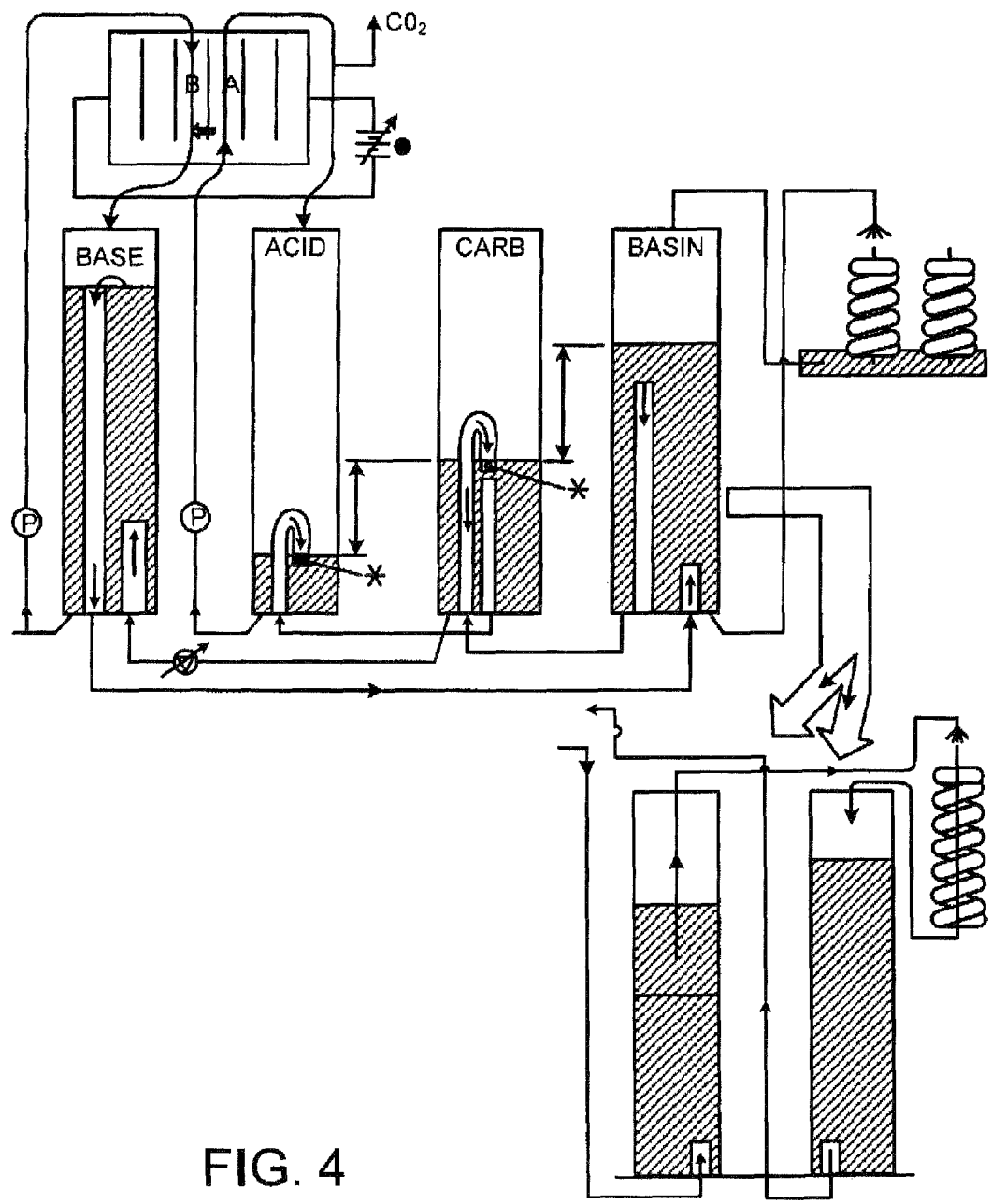
FIG. 4 is a schematic of an apparatus of the present invention having an electrodialysis cell according to one embodiment of the present disclosure.

In another aspect of the present invention shown in FIG. 4, $CO_2$ is captured using ion exchange materials and concentrated using an electrodialysis (ED) cell. The overall process is as follows: The ion exchange resin is washed using a basic solution, such as sodium carbonate ($Na_2CO_3$), preferably having a pH of 11-12. The resulting effluent, which in the example of a sodium carbonate wash will be primarily sodium bicarbonate ($NaHCO_3$), will preferably have a pH of 9-10. The effluent is then supplied to the acid side of an ED cell, where the reaction is controlled through bipolar and cationic membranes. After an initial run, the acidic side of the cell stabilizes at a near neutral pH, at which point $CO_2$ evolves and is captured. Osmotic pressure drives water towards the base side of the cell. The basic solution is maintained near a pH of 12 and may also be used to replenish the wash fluid.

Figure 5:
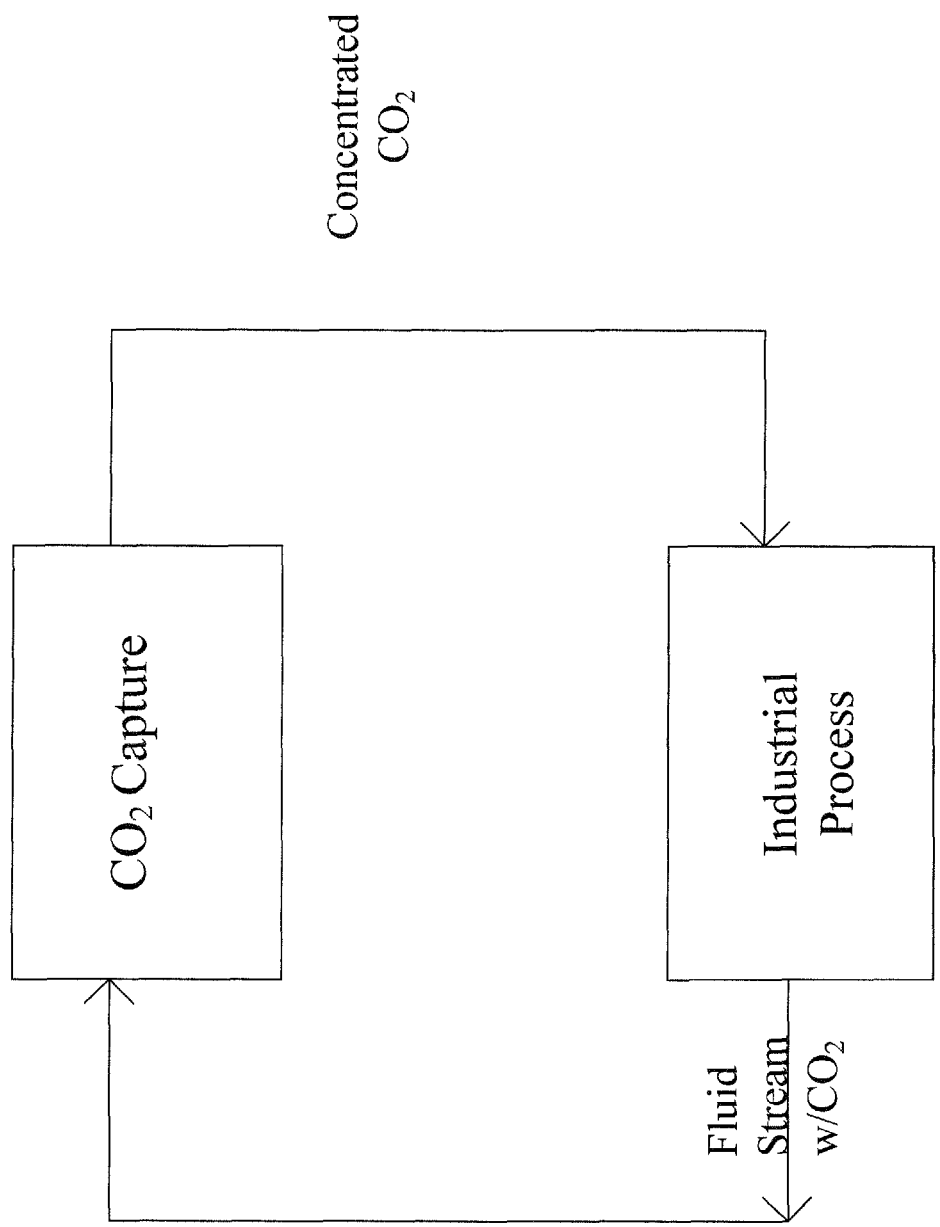
FIG. 5 is a schematic showing a system for capturing $CO_2$ in accordance with the present disclosure wherein the $CO_2$ capture device works in tandem with an industrial process to create an essentially carbon neutral system.

In another exemplary embodiment shown in FIG. 5, the present invention provides a system that is substantially carbon neutral, wherein an air capture device, such as those described herein, collects $CO_2$ that is released by an industrial process employing $CO_2$ as described above. For example, such processes include the use of $CO_2$ as a refrigerant, as a dry cleaning agent or other solvent, as a fire suppression material, as an oxidation preventing shield-gas in welding or electronics manufacture, as an alternative to sandblasting, e.g., for smoothing, or paint or rust removal, as a freezing agent in food processing, or any other process where $CO_2$ is utilized and is later released to the atmosphere. The system effectively creates a loop that is substantially carbon neutral. The air capture device may, for example, be connected the HVAC system of a building where $CO_2$ is released by processes therein. With the present invention, $CO_2$ is captured, concentrated and recycled for reuse on site.

The invention also may be used to generate carbon credits. Thus, a manufacturer may extract $CO_2$, and obtain a carbon credit which may be traded or sold, and then use the extracted $CO_2$ in a secondary process, eliminating the cost of purchasing or generating $CO_2$ for the secondary process.

Another aspect of the present disclosure provides an apparatus and method for using captured $CO_2$ to attract $CO_2$ sensitive insects, such as mosquitoes. It is known that certain insect pests like mosquitoes are attracted to sources of $CO_2$, which for them is a way to find a potential victim. In recent years lures have been developed for mosquitoes that release $CO_2$ in the environment in order to attract mosquitoes and potentially other insects. A drawback of most of these devices is that they require gas cartridges of $CO_2$ or natural gas, propane or butane to produce $CO_2$. In related applications it has been shown how certain ion exchange materials can be used to absorb $CO_2$ when they are in a dry state and release it again when they get wet. Here an application of such a material is described wherein the controlled $CO_2$ release is used to attract mosquitoes to a device at certain times while at other times the device recharges its $CO_2$ stores.

Figure 6:
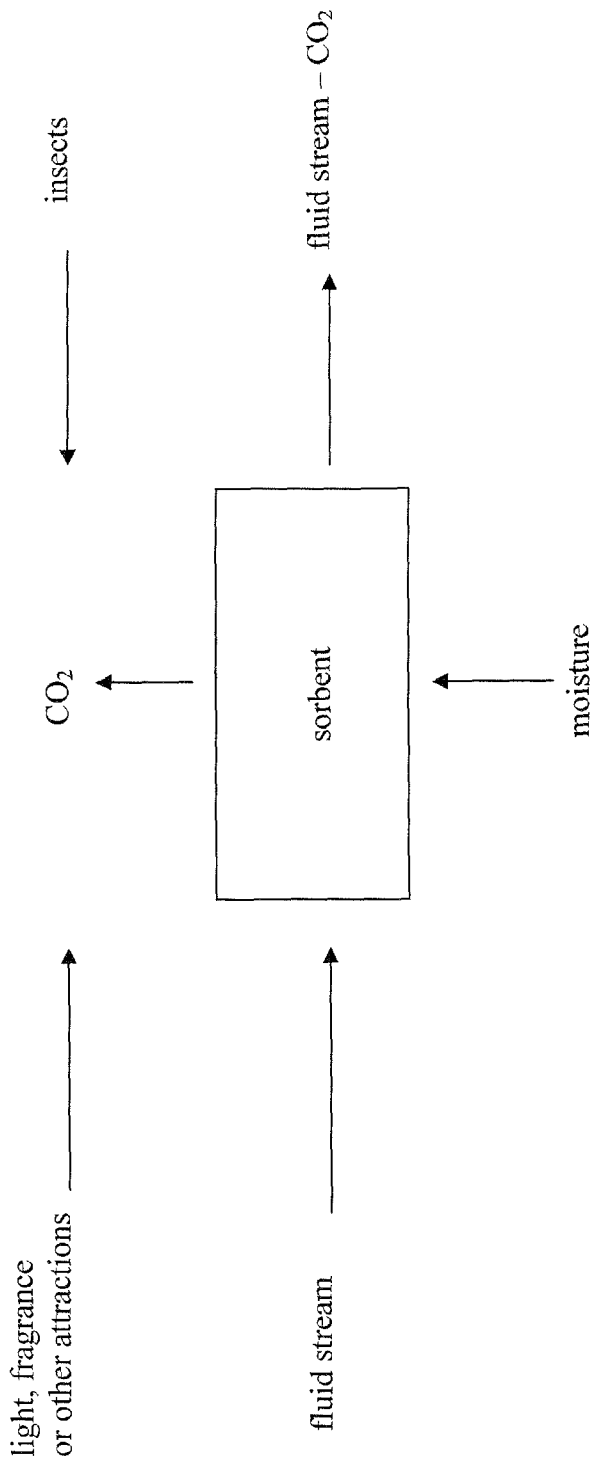
FIG. 6 is a schematic of a method and apparatus for luring CO2-sensitive insects to a desired location according to one aspect of the present disclosure.

Referring to FIG. 6, his aspect of the present disclosure describes a method of luring $CO_2$ attracted insects by using a $CO_2$ capture resin that when dry will collect $CO_2$ from the air and release it again when exposed to moisture. A number of such materials have been described in previous disclosures. This disclosure describes how these resin materials can be used to lure mosquitoes to the device at certain times.

It is possible to expose an amount of resin to air so as to load it with $CO_2$. When the device is activated, e.g. in the evening the resin is exposed to humid air, or is directly wetted for example by a small water spray. As a result the resin will begin releasing $CO_2$ therefore creating an environment that will attract mosquitoes. One implementation, for example, would be a small container filled with polymer strands of the ion exchange resins and similar materials that can be used to absorb $CO_2$. The purpose of the $CO_2$ release is to attract certain insects, like mosquitoes that are attracted by $CO_2$.

The device exposes resin to the air, and containing the resin in a way that is protected from water and rain. During times the device is inactive, it is dry and the resin will collect $CO_2$. The device includes a means of applying moisture to the resin material Moisture application could be achieved by spraying water onto the resin surface, by wicking water into a woven wick that contains the resin material, or by any other means known in the art.

The device acts as a lure to attract mosquitoes away from people. In this case the device can be completely open, because no part needs to be kept away from people. In another implementation the device includes means of killing the pest once it enters the device. This includes but is not limited to electric discharges, or by contact insecticides embedded into the resin matrix.

It is possible to combine the $CO_2$ lure with other means of attracting insects, including insects that do not respond to the presence of $CO_2$. These means include, but are not limited to light and heat sources, sounds, odors or pheromones. Devices of this nature can be designed for indoor and outdoor use. Indoor use in malaria regions may help suppress the incidence of mosquitoes and hence malaria.

Another aspect of the present disclosure relates to the capture and release of gases generated by the ripening and preservation of fruits and vegetables. Many produce items, i.e., fruits and vegetables, are often stored in a temperature-controlled environment in order to control the ripening process. Methods for the packaging and shipping of such fruits and vegetables have been developed to maximize the amount of time that the produce may be stored. Many methods for storing and ventilating produce are known that provide various types of bags and containers, including gas permeable membranes, that allow some control of the exposure of the produce to gases such as oxygen, ethylene, and carbon dioxide. However, these methods do not provide optimal storage conditions and long-term storage options are still desired.

U.S. Patent Publication No. 2008/0008793, incorporated by reference herein, discloses a method for storing bananas in a controlled environment where oxygen and carbon dioxide levels are optimized in addition to the temperature. Longer periods of storage may be achieved in this environment and improved flavor characteristics may be achieved. The reference fails, however, to discuss how such levels would be reached and maintained.

This aspect of the present disclosure provides a method for to stabilizing the $CO_2$ in a room at any level between 5 ppm and 100,000 ppm. The invention also serves to achieve a low absolute humidity (usually below 25 ppt of water vapor, preferably below 15 ppt, with improved performance as the absolute humidity drops even lower).

Figure 7:
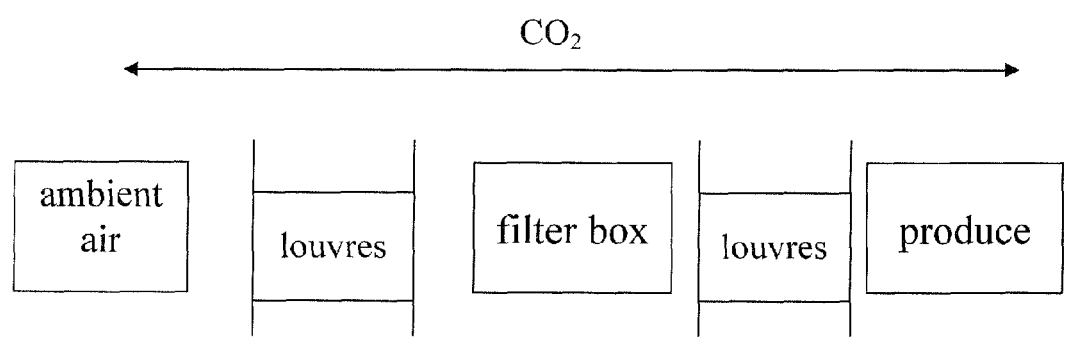
FIG. 7 is a schematic of a method and apparatus for luring CO2-sensitive insects to a desired location according to one aspect of the present disclosure.

Referring to FIG. 7, the method comprises circulating air through a filter box that follows one of the methods for $CO_2$ absorption describes in one of our aforesaid previous applications. For example, the filter may employ an ion exchange resin that is subject to a humidity swing to absorb $CO_2$ at the partial pressure representing the desired $CO_2$ level. The apparatus may include a plurality of such filters operating, wherein each filter will run until the $CO_2$ uptake rate has slowed down to a predetermined level at which we consider the resin to be essentially fully loaded. This will probably by less than the maximum loading for the resin that can be physically be achieved, but the predetermined level may be optimized for performance at some lower level to improve the collective uptake rate. The uptake rate of the resin will depend primarily on absolute humidity and to some extent on temperature, and can approach one $CO_2$ per positive elementary fixed charge in the resin.

Once the resin is loaded the air intake is closed or the resin filter may be moved into a separate chamber. A humidity swing regeneration step follows. Regeneration is accomplished by a change in temperature and absolute humidity, or by wetting the resin, e.g., as described, for example, in U.S. Pat. Nos. 4,711,645; 5,318,758; 5,914,455; 5,980,611; 6,117,404; and co-pending U.S. application Ser. No. 11/683,824, and PCT Application Ser. No. PCT/US08/82505. Wetting can be accomplished by either dipping the resin into DI or condensation water; by spraying or flowing such water over the resin, (such condensation water may be available from the refrigeration unit operating the storage facility, and may be augmented by condensation water recovered from our unit); by generating steam in a blast of warm air that results in water condensation on the resin material; or by exposing the resin to warm moist air (such warm air may be available from the hot side of the refrigeration unit, it may already be moist or need additional moisture.) If the moisture is added as humidity or by generating steam, it is not necessary to use DI or condensation water.

The moist air loaded with $CO_2$ is then purged from the unit. Heat and water may be recovered in a heat exchange unit that reduces heating demand and water consumption.

The present disclosure as discussed above may be used to cover a range of applications from extremely low levels of $CO_2$ to extremely high levels of $CO_2$. It is in principle possible to remove $CO_2$ from a gas stream that contains $CO_2$ far in excess of the levels discussed above. Levels around 1 to 10 volume percent could easily be accommodated, and operating above about 10 volume percent $CO_2$ is also possible. It is advantageous for this design to operate at temperatures below about 15° C., because the loading and unloading characteristics of the resin improve under these conditions.

Alternative options at elevated levels of $CO_2$ include the use of activated carbon, the use of zeolites, the use of weak based amine, or other physical sorbents such as actuated alumina for $CO_2$ capture instead of ion exchange resin.

In broad aspect the present invention provides a method and apparatus for the extraction of a contaminant from a gas stream. The present invention will be described in reference to a method and apparatus for capturing $CO_2$ from ambient air; however, the invention is also applicable to handling exhaust air or other gas streams and may be used to capture hydrogen sulfide, ammonia, or other common contaminants from such gas streams.

In co-pending PCT International Patent Application Ser. No. PCT/US07/84880; U.S. Provisional Patent Application Ser. No. 60/985,586, assigned to a common assignee and incorporated by reference herein, we discuss a $CO_2$ capture process that utilizes a humidity swing to regenerate a sorbent, releasing a mixture of $CO_2$ and water vapor. The water vapor may be removed from the mixture by compression or cooling, either of which will cause the water vapor to condense and precipitate out of the mixture.

To perform the humidity swing, it often is useful to expose the sorbent to low pressure water vapor. In order to achieve the required minimum water vapor pressure, it is may be necessary to operate above ambient temperatures as the maximum water vapor pressure is significantly dependent on temperature. To that end, the aforementioned co-pending applications discuss how to transfer heat to loaded sorbents that need to be inserted into an environment that is at a higher temperature.

In regenerating the sorbent it is necessary to dry the resin material. This opens an opportunity to combine such system with a vacuum distillation system, and use the heat of evaporation that is released when the material is drying to remove heat from the condenser inside the vacuum distillation system. Whereas the recovery of the $CO_2$ in most applications requires entering the resin material into a vacuum chamber, the present invention also may be used to drive a complimentary distillation process.

As explained in the aforementioned co-pending applications, the $CO_2$ sorbent is often an anionic exchange resin, but here we intend to consider all humidity-sensitive $CO_2$ sorbents that can absorb carbon dioxide from the air when they are dry and release carbon dioxide when they have been exposed to humidity in the form of liquid water and/or partial pressures of water vapor which exceed those at ambient conditions. We will generally refer to such materials as water-sensitive $CO_2$ sorbents.

Vacuum distillation is a standard method of creating fresh water from a brine, such as seawater, brackish water or other salt rich brines pumped from underground. For purposes of this disclosure, brine is also used to refer to contaminated water that is otherwise unsuitable as fresh water, such as for example, waters contaminated with biological waste materials. Thus, the term "brine" encompasses all waters contaminated with materials from which water can be separated by vacuum distillation.

Vacuum distillation begins with a chamber that has been at least partially evacuated. Brine is introduced into the chamber and is separated into two components: concentrated brine and fresh water product. There are many ways to supply a fluid into a vacuum chamber that are known to practitioners of the state of the art. By adding and subtracting from the vacuum chamber equal volumes of incompressible fluid it is possible to design a continuous flow system that requires only minimum amount of mechanical work.

The apparatus comprises a vacuum chamber that is divided into at least two parts; an evaporator unit and a condenser unit. As brine is introduced into the evaporator unit, it is allowed to evaporate. In this manner the water vapor becomes separated from the contaminants in the brine. The water vapor is then passed to a condenser unit, where it is allowed to condense. It is necessary to remove heat of condensation to keep from impeding further condensation in the condenser unit. This heat may be passed to the evaporator unit, enabling the evaporation to occur, by counterflow or some other method.

The evaporator unit, which is initially evacuated, fills with water vapor. The equilibrium partial pressure over the brine in the evaporator unit is a function of the temperature and of the salt content of the brine. The equilibrium partial pressure over the condensate in the condenser unit is a function of the temperature. At equal temperature, the equilibrium partial pressure over the condensate is slightly higher than over the brine. Thus, in a system with constant temperature the brine would gradually dilute itself with water extracted from the condensate. The system left to itself would operate in reverse, just as saltwater will become more dilute when it is separated from fresh water with a semi-permeable osmotic membrane.

One way to condense the water vapor in the condenser unit is to raise the pressure, wherein the water vapor will condense at ambient temperatures. This may be accomplished using a compressor to drive up the pressure. The heat of condensation will cause the temperature to rise in the condenser unit, wherein the heat deposited by the condensation can then be transferred to the evaporator unit. The compression acts in effect as a heat pump which transfers heat from the brine to the condensate, and a return heat flow balances out the total heat fluxes inside the system.

Where compression is used to condense the water out of the resulting gas mixture, the heat produced by that process can be transferred to the sorbent to raise its temperature as required. Alternatively, the heat required to drive the sorbent to the requisite temperature can also be derived from the condensation of water that has been allowed to evaporate at ambient conditions.

Another approach is to maintain by some other system a temperature gradient between the evaporator unit and the condenser unit, which is enough to cause a gradient in the equilibrium partial pressure that causes vapor to flow from the evaporator unit to the condenser unit. In order to maintain such a temperature differential, it is necessary to provide the heat of evaporation on the evaporator unit, and remove the heat of condensation on the condenser unit of the chamber. The required temperature differences are small; a few degrees between the evaporator and the condensate are sufficient. Operational temperatures can be low and could be well within the range of ambient temperatures, particularly in warmer climates.

One way of establishing the temperature gradient is to generate heat and transfer it to the evaporator. Another way of establishing the temperature gradient is to actively remove heat on the condenser unit. This requires a heat exchange system that removes heat from the condensate. In such an operation of the device, the temperature of the brine is higher than that of the condenser unit the heat is passed through and cannot be recovered within the system. In principle it is possible to couple one or more additional heat pumps to the system, which pumps the heat removed at the condenser unit and returns it to the evaporation side.

In combination with the $CO_2$ capture system described above, the water vapor is evaporated from the brine and is partly absorbed onto the resin. This will release a substantial portion of the $CO_2$ or other targeted contaminant from the sorbent. When this step is performed in a vacuum chamber, the atmosphere of the chamber will be filled primarily with water vapor and $CO_2$. The vacuum chamber will also aid in the evaporation of the water vapor in the brine. The concentrated brine is then removed and the water is then condensed out of the $CO_2$. Thus, the present invention produces a distilled water stream as well as concentrated $CO_2$.

Providing heat to the drying resin is advantageous and one can therefore integrate a heat exchange system operating between the drying resin collector and the condenser inside the vacuum system. In a typical implementation the evaporation of the water from the resin would not produce quite enough water to make up the water losses from the system; therefore it would have to be augmented by additional brine evaporation.

Another aspect of the present disclosure provides a different process whereby ambient environmental temperatures are used to maintain a constant temperature at the condenser unit, i.e. by flowing ambient air, or ambient water through the heat exchanger on the brine evaporation side, and we use additional brine, e.g. seawater, to operate an evaporative cooler that creates the temperature drop necessary to force the condensation of clean water inside the vacuum chamber. The amount of seawater that needs to be evaporated on the outside of the chamber to maintain a low temperature is approximately equal to the amount of brine that is converted in the vacuum distiller.

The system disclosed herein comprises a vacuum chamber with means of introducing and removing a brine, with means for removal of clean water condensate, with internal surfaces on which the brine is allowed to evaporate, and surfaces of a lower temperature where the water vapor is allowed to condense. The surfaces on which the brine is evaporating are in close contact with a heat exchanger that provides the necessary heat to maintain evaporation. It is advantageous to use free heat, i.e., heat from the ambient environment, which may have been augmented by heat, e.g. from sunshine, or, e.g. waste heat. The surfaces on which water vapor is allowed to condense are in close contact with a heat exchanger that uses additional brine to provide evaporative cooling required to force the condensation.

In the above embodiment, brine is consumed both inside and outside the chamber. The maximum acceptable concentration of the discharge brine will limit the amount of evaporation that is acceptable. The rate of consumption in both cases is similar. The two waste streams can be combined and mixed for return to the ocean or brine reservoir. The returned concentrated brine is slightly cooler than ambient temperatures.

Where ocean water or any water from a large body of water is used, it is not unusual for the input water is already cooler than ambient temperatures. In this case, it is possible to take advantage of the additional cooling power derived from the cool water that is in the system.

In addition, one might use a $CO_2$ membrane that separates $CO_2$ from nitrogen and oxygen. One option would be to use a carbonic anhydrase based membrane separation technology. Of particular utility are membranes with similar properties to the ion exchange resin discussed more fully in our other applications; (see Appendix A). The thin resin membrane would transfer $CO_2$ according to a pressure gradient in $CO_2$ and against a pressure gradient in water vapor. The two combined create a net flow of $CO_2$ across the membrane and thus by keeping the outside of the membrane wet or in high humidity one would create two chemical potentials that will drive $CO_2$ across the membrane.

Finally, there is a great synergy with the climate control of the current chamber. The $CO_2$ management is preferably integrated with de-humidification, or humidification of the air as the case may be, and it may also be integrated with the temperature control and AC handling of the air. The $CO_2$ stabilization unit, shares the air handling and blowing equipment with the other tasks, and it may be built into the same set of ducts. It can take advantage of heat and condensation water produced in the refrigeration unit.

The present disclosure in another aspect provides an additional use for extracted $CO_2$. According to the present invention, the extracted $CO_2$ is employed to neutralize carbonic acid. The present invention takes advantage of the fact that in sequestration, if one can drive the partial pressure of $CO_2$ up by about a factor of about 100, the concentrated $CO_2$ may then be injected into alkaline brines, to neutralize the brine.

The resins disclosed in our previous U.S. Provisional Patent Appln. 60/985,586 and PCT International Patent Appln. Serial No. PCT/US08/60672, assigned to a common assignee, make it possible to capture $CO_2$ from the air and drive it off the sorbent with no more than excess water vapor. It also is possible to wet the resin directly with liquid water and form a carbonate, and transfer the carbonate in a second step through a membrane between the two fluids. However, in most cases, it is preferable to create a concentrated $CO_2$ gas that then can be transferred directly into a more alkaline brine. Here again we can make direct contact between the gas and the brine, or keep them separated by a hydrophobic, porous membrane.

There are many applications where one has access to alkaline underground brines that can be used to drive a humidity swing with ionic exchange sorbents, even if their ion content make them unsuitable for direct contact with the resin. The present invention takes advantage of the humidity swing and transfers the $CO_2$ through the gas phase. Alternatively, hydrophobic membranes may be used to create a gas phase interface between two liquids, or between a liquid and a gas. If the brine covers one side of the membrane it is possible to pull $CO_2$ gas through the membrane without bringing contaminant ions in contact with the sorbent resin.

A particular application of this technology can be realized where some other industrial process has created a highly alkaline waste stream that needs to be neutralized before disposal. In that case, we can introduce carbonic acid, which will either cause the precipitation of insoluble carbonates, or produce soluble but neutral carbonate salts. Similar processes are disclosed in (PCT) Publication Number WO/2005/047183. As an example, consider waste streams from bauxite processing, e.g. in the Bayer process, which produces "red mud" at pH 13. According to the PCT Application cited above, between 1990 and 2003 six to seven million tons of red mud have been produced. Another example mentioned in the reference is the reprocessing or disposal of potassium hydroxide solutions from alkaline batteries. The process of the present invention would create potassium carbonate or bicarbonate producing materials that are indeed quite harmless.

In one aspect of the neutralization process according to the present disclosure, we propose to use an alkaline brine which is preferably in a temperature range between 40 and 60° C., and use the water vapor to recover $CO_2$ from our resins. We then wash the $CO_2$ out of the gas mixture with the help of the alkaline brine. The heated alkaline brine will provide a high level of moisture which induces the resin to give off $CO_2$ while it at the same time prevents the $CO_2$ level from rising substantially. If operated in a vacuum the process should not be transport limited. In the presence of atmospheric pressures, however, the process could be transport limited.

One possible approach is to have the liquor be soaked up in open cell foams such as AQUAFOAM® floral retention foam as described in our PCT Published Application No. WO2006/084008. Another is to have it trickle through a packed bed that is installed parallel to the resin recovery unit and cycles gas from the recovery unit through it. Another option is to contain the resins in a tube whose outside is covered with a material that soaks up the brine. In such a design heat transfer between inside and outside the tube is optimized.

The resin, which has been saturated with $CO_2$ in ambient air, is brought into a chamber connected to a second chamber containing wetted surfaces over which the brine flows. The brine will establish a high level of humidity and the resulting high humidity air is blown over the sorbent material. In one aspect of this invention this exchange will occur with humid air entering the chamber. In another aspect, residual air in the chamber is at least partially removed by evacuation prior to running water vapor through the chamber. As the water vapor is circulated between the wetted surfaces and the sorbent material, it carries $CO_2$ that is released to the alkaline brine where it is absorbed into the brine. In this implementation the resin functions to speed up the transfer of $CO_2$ from ambient air into the alkaline brine. Further acceleration of the transfer of $CO_2$ may be achieved with other materials, such as, for example, with carbonic anhydrase that thereby would open the use of brines with relatively low levels of alkalinity e.g with a pH of 8-11. In this range one could even use seawater, even though the accelerated acidification of seawater would in many cases be counter-productive. However, this would not be the case, for example, where the source of an alkaline brine is an underground aquifer, from which brine is removed and to which it is returned once the $CO_2$ is absorbed. The brine could also be water that has been exposed to alkaline mineral rocks such as basalt or peridotite or serpentinite rock. For example, one could percolate the water through a pile of serpentine tailings or other tailings that can release alkalinity.

The use of serpentine tailings to increase alkalinity is known in the art. Alternatively, the serpentine could be mined for this purposes It also is possible in some formations to inject water into alkaline underground systems for the purpose of enriching it with base cations. The presence of $CO_2$ in the water may speed up this process.

In the case of serpentine and olivine as well as basalt, this particular use of mineral sequestration would likely result in the precipitation of magnesium and/or calcium carbonate. The advantage of this method over previous attempts to directly sequester $CO_2$ from the atmosphere is that the $CO_2$ concentrations can be enriched by about a factor of 100, which will greatly help with the reaction kinetics.

Another source of alkalinity could be $Mg(OH)_2$ that has resulted from the processing of serpentine and olivine.

It is also possible to use the $CO_2$ to dissolve calcium carbonate rock that then can be put into the ocean as calcium bicarbonate. In this example it is possible to directly use seawater to drive the dissolution, and the presence of carbonic anhydrase may speed up this process dramatically. See, e.g. PCT International Patent Appln. Serial No. PCY/US08/60672, assigned to a common assignee, for a discussion of the use of carbonic anhydrase to accelerate the $CO_2$ capture process.

The dissolution of limestone with air captured $CO_2$ is analogous to a process in which the $CO_2$ comes from a power plant. The present invention provides a substantial advantage over a power plant in that we do not have to bring enormous amounts of lime stone to a power plant, or distribute the $CO_2$ from a power plant to many different processing sites, but that we can instead develop a facility where seawater, lime and $CO_2$ from the air come together more easily. One specific implementation would be to create a small basin that is periodically flushed with seawater. The $CO_2$ is provided by air capture devices located adjacent to or even above the water surface. Of particular interest are sites where limestone or other forms of calcium carbonate (such as empty mussel shells) are readily available as well. If we have calcium carbonate, seawater and air capture devices in one place, we can provide a way of disposing of $CO_2$ in ocean water without raising the pH of the water.

Indeed, it is possible to install such units adjacent a coral reef area by bringing additional limestone to the site or by extracting limestone debris near the reef. If the units operate in a slight ocean current upstream of the reef, they can generate conditions that are more suitable to the growth of the coral reef Growth conditions can be improved by raising the ion concentration product of $Ca^{++}$ and $CO_3^{--}$. This product governs the rate of coral reef growth.

It should be emphasized that the above-described embodiments of the present device and process, particularly, and "preferred" embodiments, are merely possible examples of implementations and merely set forth for a clear understanding of the principles of the invention. Many different embodiments of the invention described herein may be designed and/or fabricated without departing from the spirit and scope of the invention. All these and other such modifications and variations are intended to be included herein within the scope of this disclosure and protected by the following claims.

Therefore the scope of the invention is not intended to be limited except as indicated in the appended claims.

APPENDIX A

| | |
|---|---|
| WRIGHT 04.01 PCT | PCT/US05/29979 |
| GLOBAL 05.01 | 11/346,522 |
| GLOBAL 05.01 PCT | PCT/US06/03646 |
| GLOBAL 05.01-P | 60/649,341 |
| GLOBAL 05.02 PCT | PCT/US06/29238 |
| GLOBAL 05.02-P | 60/703,098 |
| GLOBAL 05.03-P | 60/703,099 |
| GLOBAL 05.04-P | 60/703,100 |
| GLOBAL 05.05-P | 60/703,097 |
| GLOBAL 05.06-P | 60/704,791 |
| GLOBAL 05.07-P | 60/728,120 |
| GLOBAL 06.01-P | 60/780,466 |
| GLOBAL 06.01/06.03 | 11/683,824 |
| GLOBAL 06.01/06.03 | PCT/US07/63607 |
| GLOBAL 06.03-P | 60/780,467 |
| GLOBAL 06.04-P | 60/827,849 |
| GLOBAL 06-.04/06.05 | 11/866,326 |
| GLOBAL 06.04/06.05 | PCT/US07/80229 |
| GLOBAL 06.05-P | 60/829,376 |
| GLOBAL 06.06 PCT | PCT/US07/084880 |
| GLOBAL 06.06-P | 60/866,020 |
| GLOBAL 07.01 PCT | PCT/US08/60672 |
| GLOBAL 07.01-P | 60/912,649 |
| GLOBAL 07.02-P | 60/912,379 |
| GLOBAL 07.03-P | 60/946,954 |
| GLOBAL 07.04 CIP-P | 60/985,596 |
| GLOBAL 07.04-P | 60/980,412 |
| GLOBAL 07.05-P | 60/985,586 |
| GLOBAL 07.06-P | 60/989,405 |
| GLOBAL 08.01-P | 61/058,876 |
| GLOBAL 08.02-P | 61/058,881 |
| GLOBAL 08.03-P | 61/058,879 |

What is claimed is:

1. A method for removing carbon dioxide from ambient air, comprising bringing the ambient air in contact with a solid sorbent comprising an ion exchange membrane material, thereby absorbing $CO_2$ from the ambient air, and returning a $CO_2$-depleted air flow to said ambient air; releasing the carbon dioxide from the solid sorbent in a concentrated form; and delivering the carbon dioxide for use in a secondary process, wherein the secondary process is selected from a group consisting of: use as a machining coolant and lubricant, use in grit blasting for smoothing or paint or rest removal, cryogenic cleaning, quick freeze processes, production and use of R744 refrigerant, use in $CO_2$ based dry-cleaning solvents, perishable shipping container pre-cooling, perishable shipping inert environment maintenance, beverage carbonation, fire suppression, plant fertilization, horticulture, agriculture, silvaculture, use in greenhouses, aquatic algae production, enhanced oil recovery, water softening, Solvay processes, use as a propellant, use as a pressurizing gas for aerosol cans, use as an inflation gas for life rafts, supercritical $CO_2$ extraction, semiconductor manufacturing, organic solvents, perfume aromatics, decaffeinating coffee or tea, supramics, pharmaceutical manufacturing, chemical production of urea, methanol, inorganic carbonates, organic carbonates, polyurethanes, paint pigments, foaming agents, carbon based fuels, synthetic fuels, fumigation of grain elevators, neutralization of alkaline waters or slurries or solid materials, and gas shields for welding or electronics manufacturing.

2. The method of claim 1, wherein the carbon dioxide is delivered to the secondary process in a gaseous state, solid state, or liquid state.

3. The method of claim 1, wherein the carbon dioxide is released from the solid sorbent by exposing the sorbent to increased humidity, by using water, humid air, or pulses of steam.

4. The method of claim 1, wherein the carbon dioxide is released from the solid sorbent using a weak liquid amine as a secondary sorbent.

5. The method of claim 1, wherein the solid sorbent is a resin, and wherein the carbon dioxide is released from the solid sorbent utilizing a humidity swing, and wherein the resin is contained in a chamber that also contains activated carbon, further comprising the step of drying out the activated carbon to capture the carbon dioxide in a concentrated form prior to delivering the carbon dioxide for use in a secondary process.

6. The method of claim 1, wherein the carbon dioxide is released from the solid sorbent by washing the solid sorbent with a wash fluid to create an effluent, placing the effluent on the acid side of an electrodialysis cell, driving the pH of the acid side of the electrodialysis cell to a neutral pH to release carbon dioxide, prior to delivering the carbon dioxide for use in a secondary process.

7. The method of claim 1, wherein the released carbon dioxide is delivered to an enclosed environment and maintained at a level that is within predetermined parameters.

8. The method of claim 7, further comprising controlling the humidity in the enclosed environment.

9. The method of claim 1, wherein said absorbing and/or said releasing steps are performed below about 15° C.

10. The method of claim 1, wherein said absorbing takes place in a plurality of chambers in sequence, each chamber comprising a $CO_2$ sorbent that is a solid sorbent, wherein said plurality of chambers comprises three chambers, N−1, N, and N+1, wherein chamber N is full of air and chambers N−1 and N+1 contain water; and further wherein said releasing step comprises wetting or an increase in humidity in a process that moves water and air such that:

(a) water from chamber N−1 moves into chamber N;
(b) air leaves chamber N;
(c) water leaves chamber N+1; and,
(d) chamber N+1 fills with air.

11. The method of claim 10, wherein said water comprises carbonate.

12. The method of claim 10, wherein water from chamber N+1 moves into a fourth chamber.

13. The method of claim 12, wherein said fourth chamber is nominally evacuated prior to the movement of water from chamber N+1.

14. The method of claim 12, wherein said fourth chamber contains water prior to the movement of water from chamber N+1.

15. The method of claim 1, wherein said solid sorbent comprises an anion exchange material.

16. The method of claim 1, wherein said solid sorbent comprises a material from which captured $CO_2$ is releasable by wetting or a swing in humidity in the absence of a thermal swing.

17. The method of claim 1, wherein said solid sorbent captures $CO_2$ when exposed to lower humidity and releases $CO_2$ when exposed to higher humidity.

18. The method of claim 1, wherein said solid sorbent comprises a strong base resin.

19. The method of claim 1, wherein said solid sorbent comprises a coating comprising a membrane that is hydrophobic and gas-permeable; and further wherein said releasing step comprises exposing said coated solid sorbent to an aqueous solution, wherein said solid sorbent is separated from said aqueous solution by said coating.

20. The method of claim 19, wherein said aqueous solution is an alkaline brine.

21. The method of claim 19, wherein said aqueous solution absorbs $CO_2$ released from said solid sorbent.

22. The method of claim 1, further comprising collecting and concentrating $CO_2$ released from said solid sorbent prior to delivering said $CO_2$ to said secondary process.

23. The method of claim 1, wherein said carbon dioxide is used in a secondary process on site.

24. The method of claim 1, wherein said $CO_2$-depleted flow has the same oxygen content as said stream of ambient air.

25. The method of claim 1, wherein the secondary process comprises luring insects to a desired location.

* * * * *